(12) United States Patent
Boehm et al.

(10) Patent No.: US 7,446,198 B2
(45) Date of Patent: Nov. 4, 2008

(54) 9-CYANO-SUBSTITUTED PERYLENE-3, 4-DICARBOXYLIC MONOIMIDES

(75) Inventors: Arno Boehm, Mannheim (DE); Peter Blaschka, Ludwigshafen (DE); Willi Helfer, Friedelsheim (DE); Dirk Hammel, Worms (DE); Peter Schlichting, Mannheim (DE); Klaus Muellen, Cologne (DE)

(73) Assignees: BASF Aktiengesellschaft, Ludwigshafen (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 544 days.

(21) Appl. No.: 10/528,475

(22) PCT Filed: Sep. 8, 2003

(86) PCT No.: PCT/EP03/09946

§ 371 (c)(1),
(2), (4) Date: Mar. 21, 2005

(87) PCT Pub. No.: WO2004/029028

PCT Pub. Date: Apr. 8, 2004

(65) Prior Publication Data

US 2006/0229385 A1 Oct. 12, 2006

(30) Foreign Application Priority Data

Sep. 20, 2002 (DE) ................ 102 43 906

(51) Int. Cl.
*C07D 221/18* (2006.01)
*C09B 3/14* (2006.01)

(52) U.S. Cl. .............. 546/38; 106/498; 106/499; 524/801

(58) Field of Classification Search .......... 546/38; 106/498, 499; 524/801
See application file for complete search history.

(56) References Cited

U.S. PATENT DOCUMENTS 5,405,962 A 4/1995 Muellen et al.
6,727,318 B1 * 4/2004 Mathauer et al. ........... 524/801

FOREIGN PATENT DOCUMENTS

| DE | 100 38 672 | 5/2002 |
|---|---|---|
| EP | 0 657 436 | 6/1995 |
| EP | 0 854 144 | 7/1998 |
| WO | 96/22331 | 7/1996 |
| WO | 96/22332 | 7/1996 |
| WO | 98/31678 | 7/1998 |
| WO | 99/40123 | 8/1999 |
| WO | 01/16109 | 3/2001 |

OTHER PUBLICATIONS

Nagao Y et al: "Synthesis and Properties of N-Alkylbromoperylene-3,4-Dicarboximides" Dyes and Pigments, Elsevier Applied Science Publishers. vol. 16, No. 1, pp. 19-25, 1991.
Kyokaishi, Shikizai: "Synthesis and reactions of perylenecarboxylic derivatives V. Syntheses of perylenedicarbonimide derivatives." vol. 49, No. 1, pp. 29 to 34, 1976. XP 000208007 (English abstract only).
Nagao Y et al: Synthesis and Reactions of Perylenecarboxylic Acid Derivatives. X. Synthesis of N-Alkyl-3,4-perylenedicarboximide. Bull.Chem.Soc.Jpn. vol. 54, pp. 1575-1576, 1981.

* cited by examiner

*Primary Examiner*—Charanjit S Aulakh
(74) *Attorney, Agent, or Firm*—Oblon, Spivak, McClelland, Maier & Neustadt, P.C.

(57) ABSTRACT

A 9-cyano-substituted perylene-3,4-dicarboxylic monoimide I

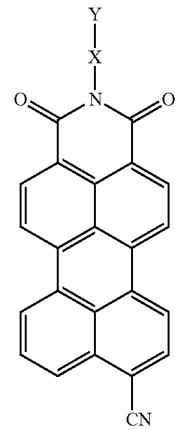

where the variables are defined in the specification.

11 Claims, No Drawings

9-CYANO-SUBSTITUTED PERYLENE-3,4-DICARBOXYLIC MONOIMIDES

The present invention relates to novel 9-cyano-substituted perylene-3,4-dicarboxylic monoimides of the general formula I

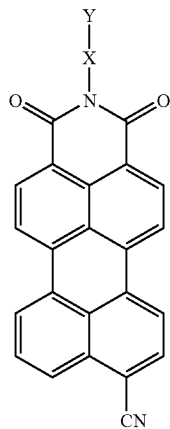

where the variables are defined as follows:

X is a chemical bond;
- $C_1$-$C_{30}$-alkylene whose carbon chain may be interrupted by one or more —O—, —S—, —$NR^1$—, —CO— and/or —$SO_2$— moieties, and which may be substituted by —$COOR^1$, —$SO_3R^1$, cyano, $C_1$-$C_6$-alkoxy, aryl which may be substituted by $C_1$-$C_{18}$-alkyl and/or $C_1$-$C_6$-alkoxy, and/or be mono- or polysubstituted by a 5- to 7-membered heterocyclic radical which is bonded via a nitrogen atom and may contain further heteroatoms and be aromatic;
- $C_5$-$C_8$-cycloalkylene whose carbon framework may be interrupted by one or more —O—, —S—, —$NR^1$—, —CO— and/or —$SO_2$— moieties and/or may be mono- or polysubstituted by $C_1$-$C_{12}$-alkyl, —$COOR^1$, —$SO_3R^1$, cyano and/or $C_1$-$C_6$-alkoxy;
- arylene or hetarylene, each of which may be mono- or polysubstituted by $C_1$-$C_{18}$-alkyl, $C_1$-$C_6$-alkoxy, cyano, —$COOR^1$, —$SO_3R^1$, —CONH—$R^1$ and/or —NH—$COR^1$;
- $C_1$-$C_{20}$-alkylarylene or -hetarylene whose alkylene group may in each case be interrupted by one or more —O—, —S—, —$NR^1$—, —CO— and/or —$SO_2$— moieties and which may in each case be mono- or polysubstituted by —$COOR^1$, —$SO_3R^1$, —$CONHR^1$, —$NHCOR^1$, cyano, $C_1$-$C_{18}$-alkyl, $C_1$-$C_6$-alkoxy and/or a 5- to 7-membered heterocyclic radical which is bonded via a nitrogen atom and may contain further heteroatoms and be aromatic;
- aryl- or hetaryl-$C_1$-$C_{20}$-alkylene, whose alkylene group may in each case be interrupted by one or more —O—, —S—, —$NR^1$—, —CO— and/or —$SO_2$— moieties and which may in each case be mono- or polysubstituted by —$COOR^1$, —$SO_3R^1$, —$CONHR^1$, —$NHCOR^1$, cyano, $C_1$-$C_{18}$-alkyl, $C_1$-$C_6$-alkoxy and/or a 5- to 7-membered heterocyclic radical which is bonded via a nitrogen atom and may contain further heteroatoms and be aromatic;

Y is a functional group Y' or a polymerizable group P;
or
X—Y together is an R radical;
Y' is amino, hydroxyl, —COOH, —$SO_3H$, chlorine or bromine;
P is a radical of the general formula II

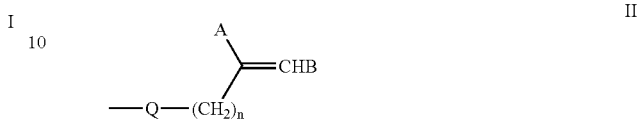

A, B are each independently hydrogen, $C_1$-$C_6$-alkyl or phenyl, or are together a cyclopentene or cyclohexene ring which contains the double bond to which A and B are bonded;
Q is a chemical bond;
- an —O—, —$NR^2$—, —S—, —OCO—, —OCOO—, —$OCONR^3$—, —$NR^3CO$—, —$NR^3COO$—, —$NR^3CONR^4$—, —CO—, —COO—, —$CONR^3$—, —$SO_2$—O—, —$SO_2NR^3$—, —O—$SO_2$— or —$NR^3SO_2$—moiety;
n is 0, 1, 2 or 3;
R is hydrogen;
- $C_1$-$C_{30}$-alkyl whose carbon chain may be interrupted by one or more —O—, —S—, —$NR^1$—, —CO— and/or —$SO_2$— moieties, and which may be substituted by cyano, $C_1$-$C_6$-alkoxy, aryl which may be substituted by $C_1$-$C_{18}$-alkyl and/or $C_1$-$C_6$-alkoxy, and/or be mono- or polysubstituted by a 5- to 7-membered heterocyclic radical which is bonded via a nitrogen atom and may contain further heteroatoms and be aromatic;
- $C_5$-$C_8$-cycloalkyl whose carbon framework may be interrupted by one or more —O—, —S— and/or —$NR^1$— moieties and/or may be mono- or polysubstituted by $C_1$-$C_6$-alkyl;
- aryl or hetaryl, each of which may be mono- or polysubstituted by $C_1$-$C_{18}$-alkyl, $C_1$-$C_6$-alkoxy, cyano, —$CONHR^5$, —$NHCOR^5$ and/or aryl- or hetarylazo, each of which may be substituted by $C_1$-$C_{10}$-alkyl, $C_1$-$C_6$-alkoxy and/or cyano;
$R^1$ is hydrogen or $C_1$-$C_6$-alkyl;
$R^2$ is hydrogen, $C_1$-$C_6$-alkyl, aryl, aryl-$C_1$-$C_6$-alkyl, $C_1$-$C_6$-alkylcarbonyl, arylcarbonyl or formyl;
$R^3$, $R^4$ are each independently hydrogen; $C_1$-$C_6$-alkyl; aryl or aryl-$C_1$-$C_6$-alkyl, each of which may be substituted by hydroxyl, halogen, $C_1$-$C_6$-alkyl and/or $C_1$-$C_6$-alkoxy;
$R^5$ is hydrogen; $C_1$-$C_{18}$-alkyl; aryl or hetaryl, each of which may be substituted by $C_1$-$C_6$-alkyl, $C_1$-$C_6$-alkoxy, halogen, hydroxyl, carboxyl and/or cyano, and also to the preparation of these 9-cyano-substituted perylene-3,4-dicarboxylic monoimides and to their use as fluorescent dyes, for coloring high molecular weight organic and inorganic materials, in particular plastics, paints, printing inks, inorganic-organic composites and oxidic layer systems, as dispersants, pigment additives for organic pigments and intermediates for the preparation of fluorescent dyes and pigment additives, for producing aqueous polymer dispersions and inkjet inks absorbing and/or emitting in the yellow region of the electromagnetic spectrum, as photoconductors in electrophotography, as coloring or color-correcting components in emissive and transflective color filters and in retroreflective components, as emitters in electroluminescence and chemiluminescence applications, as active components in fluorescence conversion, in fluorescence solar collectors, in bioluminescence arrays and also in photovoltaics and as laser dyes.

The invention further relates to the perylene-3,4-dicarboxylic anhydride, brominated or cyano-substituted in the 9-position, of the formula III

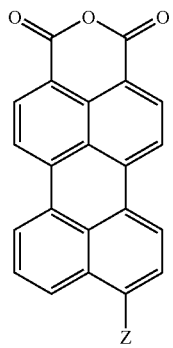

III where Z is bromine or cyano as intermediate in the preparation of the 9-cyano-substituted perylene-3,4-dicarboxylic monoimides of the formula I according to the invention.

N-substituted perylene-3,4-dicarboxylic monoimides which bear no substituents in the perylene framework and processes for preparing them are disclosed by a series of publications (for example Shikizai Kyokai Shi 49, 29 (1976), Bull. Chem. Soc. Jpn. 54, 1575 (1981) and EP-A-657 436). Although EP-A-854 144 and WO-A-98/31678 claim perylene-3,4-dicarboxylic monoimides substituted in the perylene framework and substituted perylene-3,4-dicarboxylic anhydride, excluding substitution in the 9-position in WO-A-98/31678, only the compounds unsubstituted in the perylene framework are explicitly disclosed.

Perylene-3,4-dicarboxylic monoimides substituted, including brominated, in the perylene framework are described in WO-A-96/22331 (in particular 1,7-disubstituted compounds) and WO-A-96/22332 (in particular 1,6,9-trisubstituted compounds). Dyes and Pigments 16, 19 (1991), U.S. Pat. No. 5,405,962 and WO-A-01/16109 finally relate to perylene-3,4-dicarboxylic monoimides substituted in the 9-position, although the first two publications describe exclusively brominated compounds, and cyano-substituted perylene-3,4-dicarboxylic monoimides are disclosed by none of these publications.

All known perylene-3,4-dicarboxylic monoimides absorb and emit in the orange to bluish-red color range. Representatives of this class of compounds which absorb or emit in the yellow color range, i.e. distinctly more hypsochromically, are not described in the literature and were not to be expected either as a consequence of the size of the chromophoric system for this substance class.

The synthetic routes described in EP-A-854 144 and WO-A-98/31678 for preparing perylene-3,4-dicarboxylic anhydrides (via an alkylation/arylation-hydrolysis sequence, starting from perylene-3,4-dicarboxylic monoimides unsubstituted at the nitrogen atom, or via direct partial base-induced decarboxylation of perylene-3,4:9,10-tetracarboxylic dianhydrides) are very costly and inconvenient and cannot be realized on the industrial scale. In addition, 9-bromoperylene-3,4-dicarboxylic anhydride can in principle not be prepared as a consequence of the instability of the bromine substituents under the specified basic hydrolysis and decarboxylation conditions.

The conversions described in Dyes and Pigments 16, 19 (1991) and U.S. Pat. No. 5,405,962 for selectively brominating N-substituted perylene-3,4-dicarboxylic monoimides in the 9-position in the presence of halogenated organic solvents, as a consequence of the insufficient solubility of many of the substrates to be converted, in particular of perylene-3,4-dicarboxylic anhydride itself, in these solvents at the maximum permissible reaction temperatures can be used neither universally nor for industrial batch sizes. In addition, 9-bromoperylene-3,4-dicarboxylic monoimides and their subsequent products which bear further functional groups on the imide nitrogen atom which are unstable under the bromination or nucleophilic substitution reaction conditions are in principle not accessible by the literature routes.

It is an object of the present invention to provide suitably substituted perylene-3,4-dicarboxylic monoimides having advantageous application properties which can in particular not only be incorporated readily into the particular application medium and be adaptable to this medium, but also absorb and emit at a shorter wavelength (more hypsochromically), i.e. in the yellow region of the electromagnetic spectrum, than the representatives of the substance class known hitherto.

We have found that this object is achieved by the 9-cyano-substituted perylene-3,4-dicarboxylic monoimides of the formula I defined at the outset.

Preferred 9-cyano-substituted perylene-3,4-dicarboxylic monoimides can be taken from the subclaim.

A process has also been found for preparing non- or monofunctional 9-cyanoperylene-3,4-dicarboxylic monoimides of the general formula Ia

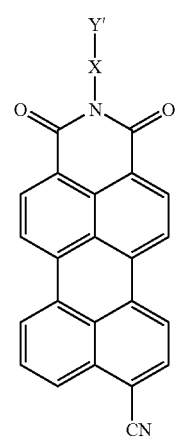

Ia where X and Y' are as defined at the outset or X—Y' together are one of the R radicals defined at the outset, which comprises a) brominating perylene-3,4-dicarboxylic anhydride in the 9-position using elemental bromine in concentrated sulfuric acid or an aliphatic monocarboxylic acid, b) reacting the 9-bromoperylene-3,4-dicarboxylic anhydride obtained in step a) with copper(I) cyanide in excess in a high-boiling inert diluent, optionally with the addition of a basic nitrogen compound or of a nitrogen heterocycle as a catalyst, and c) reacting the 9-cyanoperylene-3,4-dicarboxylic anhydride obtained in step b) with a primary amine of the general formula IV

Y'—X—NH$_2$

IV in water or an inert organic solvent, optionally with the addition of an imidation catalyst, to give the desired 9-cyanoperylene-3,4-dicarboxylic monoimide of the formula Ia.

A process has also been found for preparing 9-cyanoperylene-3,4-dicarboxylic monoimides of the general formula Ib

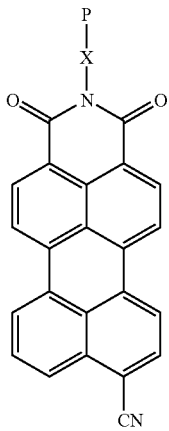

Ib which contain a group capable of free-radical polymerization and where X is as defined at the outset and P is one of the radicals of the formula II as defined at the outset where Q is —OCO— or —NHCO—, which comprises reacting a perylene-3,4-dicarboxylic monoimide of the formula Ia where Y' is amino or hydroxyl with a carbonyl chloride of the general formula V

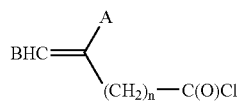

V where the variables are as defined at the outset in an inert aprotic diluent, with the addition of a nitrogen base.

Finally, a process has been found for preparing 9-cyanoperylenedicarboxylic monoimides of the general formula Ic

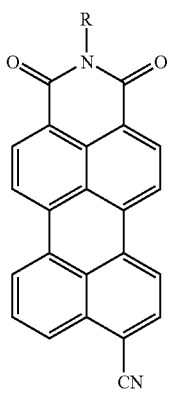

Ic where R is as defined at the outset, which comprises converting a 9-bromoperylene-3,4-dicarboxylic monoimide of the general formula VI

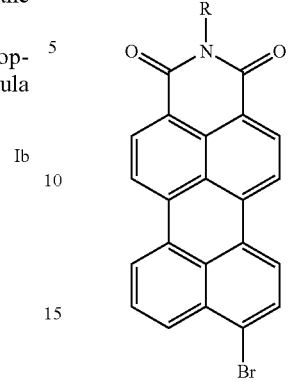

VI to the desired 9-cyanoperylene-3,4-dicarboxylic monoimide of the formula Ic by reacting with copper(I) cyanide without a diluent or in a high-boiling inert diluent, optionally with the addition of a basic nitrogen compound or of a nitrogen heterocycle as a catalyst.

Not least, perylene-3,4-dicarboxylic anhydrides, substituted in the 9-position, of the general formula III

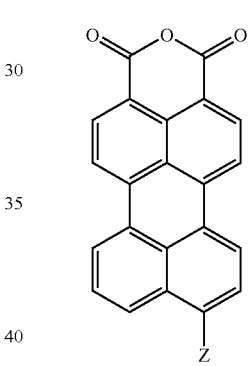

III where Z is bromine or cyano, and also the processes for preparing these perylene-3,4-dicarboxylic anhydrides have been found, which comprise selectively brominating perylene-3,4-dicarboxylic anhydride in the 9-position with elemental bromine in concentrated sulfuric acid or an aliphatic monocarboxylic acid, and reacting the resulting 9-bromoperylene-3,4-dicarboxylic anhydride IIIa with copper(I) cyanide in excess in a high-boiling inert diluent, optionally with the addition of a basic nitrogen compound or of a nitrogen heterocycle as a catalyst.

Not least, the use has been found of the 9-cyano-substituted perylene-3,4-dicarboxylic monoimides I as fluorescent dyes, for coloring high molecular weight organic and inorganic materials, in particular plastics, paints, printing inks, inorganic-organic composites and oxidic layer systems, as dispersants, pigment additives for organic pigments and intermediates for the preparation of fluorescent dyes and pigment additives, for producing aqueous polymer dispersions and inkjet inks absorbing and/or emitting in the yellow region of the electromagnetic spectrum, as photoconductors in electrophotography, as coloring or color-correcting components in emissive and transflective color filters and in retroreflective components, as emitters in electroluminescence and chemiluminescence applications, as active components in fluorescence conversion, in fluorescence solar collectors, in bioluminescence arrays and also in photovoltaics and as laser dyes.

All alkyl groups occurring in the formulae I to VI may be straight-chain or branched. When the alkyl groups are substituted, they generally have 1 or 2 substituents.

Aromatic radicals which are substituted may generally have up to 3, preferably 1 or 2, of-the substituents mentioned.

Specific examples of suitable R, $R^1$, $R^2$, $R^3$, $R^4$, $R^5$, X, Y, Q, A and B radicals (or their substituents) are as follows:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

methylene, ethylene, propylene, isopropylene, butylene, isobutylene, tert-butylene, pentylene, isopentylene, neopentylene, tert-pentylene, hexylene, 2-methylpentylene, heptylene, 1-ethylpentylene, octylene, 2-ethylhexylene, isooctylene, nonylene, isononylene, decylene, isodecylene, undecylene, dodecylene, tridecylene, isotridecylene, tetradecylene, pentadecylene, hexadecylene, heptadecylene, octadecylene, nonadecylene and eicosylene (the above terms isooctylene, isononylene, isodecylene and isotridecylene are trivial terms and stem from the alcohols obtained by the oxo process);

methoxymethyl, 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-oxapropylene, 2- and 3-oxabutylene, 2-, 3- and 4-oxapentylene, 2-, 3-, 4- and 5-oxahexylene, 2- and 3-oxa-4-methylpentylene, 2- and 4-oxa-3-methylpentylene, 2-, 3-, 4-, 5- and 6-oxaheptylene, 2-, 3-, 4-, 5-, 6- and 7-oxaoctylene, 2-, 3-, 4-, 5-, 6-, 7- and 8-oxanonylene, 3,6-dioxaheptylene, 3,6-dioxaoctylene, 4,8-dioxanonylene, 3,7-dioxaoctylene, 3,7-dioxanonylene, 4,7-dioxaoctylene, 4,7-dioxanonylene, 4,8-dioxadecylene, 3,6,9-trioxadecylene, 3,6,9-trioxaundecylene, 3,6,9-trioxadodecylene, 3,6,9,12-tetraoxatridecylene and 3,6,9,12-tetraoxatetradecylene;

methylthiomethyl, 2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-thiapropylene, 2- and 3-thiabutylene, 2-, 3- and 4-thiapentylene, 2-, 3-, 4- and 5-thiahexylene, 2- and 3-thia-4-methylpentylene, 2- and 4-thia-3-methylpentylene, 2-, 3-, 4-, 5- and 6-thiaheptylene, 2-, 3-, 4-, 5-, 6- and 7-thiaoctylene, 2-, 3-, 4-, 5-, 6-, 7- and 8-thianonylene, 3,6-dithiaheptylene, 3,6-dithiaoctylene, 4,8-dithianonylene, 3,7-dithiaoctylene, 3,7-dithianonylene, 4,7-dithiaoctylene, 4,7-dithianonylene, 4,8-dithiadecylene, 3,6,9-trithiadecylene, 3,6,9-trithiaundecylene, 3,6,9-trithiadodecylene, 3,6,9,12-tetrathiatridecylene and 3,6,9,12-tetrathiatetradecylene;

2-monomethyl- and 2-monoethylaminoethyl, 2-dimethylaminoethyl, 2- and 3- dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

N-methyl-, N-ethyl-, N-propyl-, N-isopropyl- and N-butyl-2-azapropylene, N-methyl-, N-ethyl-, N-propyl-, N-isopropyl- and N-butyl-2-azabutylene, N-methyl-, N-ethyl-, N-propyl-, N-isopropyl- and N-butyl-3-azabutylene, N-methyl-, N-ethyl-, N-propyl-, N-isopropyl- and N-butyl-2-azapentylene, N-methyl-, N-ethyl-, N-propyl-, N-isopropyl- and N-butyl-3-azapentylene, N-methyl-, N-ethyl-, N-propyl-, N-isopropyl- and N-butyl-4-azapentylene, N-methyl-, N-ethyl-, N-propyl-, N-isopropyl- and N-butyl-2-azahexylene, N-methyl-, N-ethyl-, N-propyl-, N-isopropyl- and N-butyl-3-azahexylene, N-methyl-, N-ethyl-, N-propyl-, N-isopropyl- and N-butyl-4-azahexylene, N-methyl-, N-ethyl-, N-propyl-, N-isopropyl- and N-butyl-5-azahexylene, 3-methyl-3,6-diazaheptylene, 6-methyl-3,6-diazaheptylene, 3,6-dimethyl-3,6-diazaheptylene, 3,6-diazaoctylene, 3,6-dimethyl-3,6-diazaoctylene, 3-methyl-3,6,9-triazadecylene, 6-methyl-3, 6,9-triazadecylene, 9-methyl-3,6, 9-triazadecylene, 3,6,9-trimethyl-3,6,9-triazadecylene, 3,6,9-triazaundecylene, 3,6,9-trimethyl-3,6,9-triazaundecylene, 3-methyl-3,6,9,12-tetraazatridecylene, 6-methyl-3,6,9,12-tetraazatridecylene, 9-methyl-3,6,9,12-tetraazatridecylene, 12-methyl-3,6,9,12-tetraazatridecylene and 3,6,9,12-tetramethyl-3,6,9,12-tetraazatridecylene;

propan-2-on-1-yl, butan-3-on-1-yl, butan-3-on-2-yl and 2-ethylpentan-3-on-1-yl;

propylen-2-one, butylen-2-one, butylen-3-one and 2-ethylpentylen-3-one, 2-ethylpentylen-4-one, 3-ethylpentylen-2-one and 3-ethylpentylen-4-one;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

methylene-, ethylene-, propylene-, isopropylene-, butylene-, isobutylene-, sec-butylene-, tert-butylene- and pentylenesulfonylmethylene, methylene-, ethylene-, propylene-, isopropylene-, butylene-, isobutylene-, sec-butylene-, tert-butylene- and pentylenesulfonylethylene, methylene-, ethylene-, propylene-, isopropylene-, butylene-, isobutylene-, sec-butylene-, tert-butylene- and pentylenesulfonylpropylene, methylene-, ethylene-, propylene-, isopropylene-, butylene-, isobutylene-, sec-butylene-, tert-butylene- and pentylenesulfonylisopropylene, methylene-, ethylene-, propylene-, isopropylene-, butylene-, isobutylene-, sec-butylene-, tert-butylene- and pentylenesulfonylbutylene, methylene-, ethylene-, propylene-, isopropylene-, butylene-, isobutylene-, sec-butylene-, tert-butylene- and pentylenesulfonylisobutylene, methylene-, ethylene-, propylene-, isopropylene-, butylene-, isobutylene-, sec-butylene-, tert-butylene- and pentylenesulfonyl-sec-butylene, methylene-, ethylene-, propylene-, isopropylene-, butylene-, isobutylene-, sec-butylene-, tert-butylene- and pentylenesulfonyl-tert-butylene, methylene-, ethylene-, propylene-, isopropylene-, butylene-, isobutylene-, sec-butylene-, tert-butylene- and pentylenesulfonylpentylene, 1,2-bis(methylenesulfonyl)ethane, 1,2- and 1,3- bis(methylenesulfonyl)propane, 1,2-, 1,3- and 1,4-bis(methylenesulfonyl)butane, 1,2-, 1,3-, 1,4- and 1,5-bis(methylenesulfonyl)pentane, 1,2-bis(ethylenesulfonyl)ethane, 1,2- and 1,3-bis(ethylenesulfonyl)propane, 1,2-, 1,3- and 1,4-bis(ethylenesulfonyl)butane, 1,2-, 1,3-, 1,4- and 1,5-bis(ethylenesulfonyl)pentane, 1,2-bis(propylenesulfonyl)ethane, 1,2- and 1,3-bis(propylenesulfonyl)propane, 1,2-, 1,3- and 1,4-bis(propylenesulfonyl)butane, 1,2-, 1,3-, 1,4- and 1,5-bis(propylenesulfonyl)pentane;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 3-hydroxypropyl, 1-hydroxyprop-2-yl, 2- and 4-hydroxybutyl, 1-hydroxybut-2-yl and 8-hydroxy-4-oxaoctyl;

cyanomethyl, 2-cyanoethyl, 3-cyanopropyl, 2-methyl-3-ethyl-3-cyanopropyl, 7-cyano-7-ethylheptyl and 4,7-dimethyl-7-cyanoheptyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

formylamino, acetylamino, propionylamino and benzoylamino;

chlorine, bromine and iodine;

phenyl, 1- and 2-naphthyl, 2- and 3-pyrryl, 2-, 3- and 4-pyridyl, 2-, 4- and 5-pyrimidyl, 2-pyrazyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1,2-, 1,3- and 1,4-phenylene, 1,2-, 2,3-, 1,4-, 1,5-, 2,6- and 1,8-naphthylene, 2,5- and 3,4-pyrrylene, 2,3-, 2,4-, 2,5-, 2,6- and 3,5-pyridylene, 2,4- and 2,5-pyrimidylene, 2,3-, 2,5- and 2,6-pyrazylene, 3,5-pyrazolylene, 1,2-, 1,4-, 1,5-, 2,4- and 2,5-imidazolylene, 2,4- and 2,5-thiazolylene, 3,5- and 3,6-(1,2,4-triazylene), 2,4-(1,3,5-triazylene), 3,5-, 3,6-, 3,8- and 5,8-quinaldylene, 3,5-, 3,6-, 3,8- and 5,8-quinolinylene, 2,4- and 2,5-benzimidazolylene and 1,3-, 1,4-, 1,5- and 1,6-isoquinolylene;

2-, 3- and 4-methylphenyl, 2,3-, 2,4-, 2,5-, 3,5- and 2,6-dimethylphenyl, 2,4,6-trimethylphenyl, 2-, 3- and 4-ethylphenyl, 2,3-, 2,4-, 2,5-, 3,5- and 2,6-diethylphenyl, 2,4,6-triethylphenyl, 2-, 3- and 4-propylphenyl, 2,3-, 2,4-, 2,5-, 3,5- and 2,6-dipropylphenyl, 2,4,6-tripropylphenyl, 2-, 3- and 4-isopropylphenyl, 2,3-, 2,4-, 2,5-, 3,5- and 2,6-diisopropylphenyl, 2,4,6-triisopropylphenyl, 2-, 3- and 4-butylphenyl, 2,3-, 2,4-, 2,5-, 3,5- and 2,6-dibutylphenyl, 2,4,6-tributylphenyl, 2-, 3- and 4-isobutylphenyl, 2,3-, 2,4-, 2,5-, 3,5- and 2,6-diisobutylphenyl, 2,4,6-triisobutylphenyl, 2-, 3- and 4-sec-butylphenyl, 2,3-, 2,4-, 2,5-, 3,5- and 2,6-di-sec-butylphenyl and 2,4,6-tri-sec-butylphenyl, 2-, 3- and 4-tert-butylphenyl, 2,3-, 2,4-, 2,5-, 3,5- and 2,6-di-tert-butylphenyl, 2,4,6-tri-tert-butylphenyl; 2-, 3- and 4-methoxyphenyl, 2,3-, 2,4-, 2,5-, 3,5- and 2,6-dimethoxyphenyl, 2,4,6-trimethoxyphenyl, 2-, 3- and 4-ethoxyphenyl, 2,3-, 2,4-, 2,5-, 3,5- and 2,6-diethoxyphenyl, 2,4,6-triethoxyphenyl, 2-, 3- and 4-propoxyphenyl, 2,3-, 2,4-, 2,5-, 3,5- and 2,6-dipropoxyphenyl, 2-, 3- and 4-isopropoxyphenyl, 2,3-, 2,4-, 2,5-, 3,5- and 2,6-diisopropoxyphenyl and 2-, 3- and 4-butoxyphenyl; 2-, 3- and 4-chlorophenyl, and 2,3-, 2,4-, 2,5-, 3,5- and 2,6-dichlorophenyl; 2-, 3- and 4-hydroxyphenyl and 2,3-, 2,4-, 2,5-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl;

3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

2-methyl-1,3-, -1,4-, -1,5- and -1,6-phenylene, 2,3-dimethyl-1,4-, -1,5- and -1,6-phenylene, 2,4-dimethyl-1,3-, -1,5- and -1,6-phenylene, 2,5-dimethyl-1,3-, -1,4- and -1,6-phenylene, 2,4,5-trimethyl-1,3- and -1,6-phenylene, 2,4,6-trimethyl-1,3-phenylene, 2-ethyl-1,3-, -1,4-, -1,5- and -1,6-phenylene, 2,3-diethyl-1,4-, -1,5- and -1,6-phenylene, 2,4-diethyl-1,3-, -1,5- and -1,6-phenylene, 2,5-diethyl-1,3-, -1,4- and -1,6-phenylene, 2,4,5-triethyl-1,3- and -1,6-phenylene, 2,4,6-triethyl-1,3-phenylene, 2-propyl-1,3-, -1,4-, -1,5- and -1,6-phenylene, 2,3-dipropyl-1,4-, -1,5- and -1,6-phenylene, 2,4-dipropyl-1,3-, -1,5- and -1,6-phenylene, 2,5-dipropyl-1,3-, -1,4- and -1,6-phenylene, 2,4,5-tripropyl-1,3- and -1,6-phenylene, 2,4,6-tripropyl-1,3-phenylene, 2-isopropyl-1,3-, -1,4-, -1,5- and -1,6-phenylene, 2,3-diisopropyl-1,4-, -1,5- and -1,6-phenylene, 2,4-diisopropyl-1,3-, -1,5- and -1,6-phenylene, 2,5-diisopropyl-1,3-, -1,4- and -1,6-phenylene, 2,4,5-triisopropyl-1,3- and -1,6-phenylene, 2,4,6-triisopropyl-1,3-phenylene, 2-butyl-1,3-, -1,4-, -1,5- and -1,6-phenylene, 2,3-dibutyl-1,4-, -1,5- and -1,6-phenylene, 2,4-dibutyl-1,3-, -1,5- and -1,6-phenylene, 2,5-dibutyl-1,3-, -1,4- and -1,6-phenylene, 2,4,5-tributyl-1,3- and -1,6-phenylene, 2,4,6-tributyl-1,3-phenylene, 2-isobutyl-1,3-, -1,4-, -1,5- and -1,6-phenylene, 2,3-diisobutyl-1,4-, -1,5- and -1,6-phenylene, 2,4-diisobutyl-1,3-, -1,5- and -1,6-phenylene, 2,5-diisobutyl-1,3-, -1,4- and -1,6-phenylene, 2,4,5-triisobutyl-1,3- and -1,6-phenylene, 2,4,6-triisobutyl-1,3-phenylene, 2-sec-butyl-1,3-, -1,4-, -1,5- and -1,6-phenylene, 2,3-di-sec-butyl-1,4-, -1,5- and -1,6-phenylene, 2,4-di-sec-butyl-1,3-, -1,5- and -1,6-phenylene, 2,5-di-sec-butyl-1,3-, -1,4- and -1,6-phenylene, 2,4,5-tri-sec-butyl-1,3- and -1,6-phenylene, 2,4,6-tri-sec-butyl-1,3-phenylene, 2-tert-butyl-1,3-, -1,4-, -1,5- and -1,6-phenylene, 2,3-di-tert-butyl-1,4-, -1,5- and -1,6-phenylene, 2,4-di-tert-butyl-1,3-, -1,5- and -1,6-phenylene, 2,5-di-tert-butyl-1,3-, -1,4- and -1,6-phenylene, 2,4,5-tri-tert-butyl-1,3- and -1,6-phenylene, 2,4,6-tri-tert-butyl-1,3-phenylene; 2-methoxy-1,3-, -1,4-, -1,5- and -1,6-phenylene, 2,3-dimethoxy-1,4-, -1,5- and -1,6-phenylene, 2,4-dimethoxy-1,3-, -1,5- and -1,6-phenylene, 2,5-dimethoxy-1,3-, -1,4- and -1,6-phenylene, 2,4,5-trimethoxy-1,3- and -1,6-phenylene, 2,4,6-trimethoxy-1,3-phenylene, 2-ethoxy-1,3-, -1,4-, -1,5- and -1,6-phenylene, 2,3-diethoxy-1,4-, -1,5- and -1,6-phenylene, 2,4-diethoxy-1,3-, -1,5- and -1,6-phenylene, 2,5-diethoxy-1,3-, -1,4- and -1,6-phenylene, 2,4,5-triethoxy-1,3- and -1,6-phenylene, 2,4,6-triethoxy-1,3-phenylene, 2-propoxy-1,3-, -1,4-, -1,5- and -1,6-phenylene, 2,3-dipropoxy-1,4-, -1,5- and -1,6-phenylene, 2,4-dipropoxy-1,3-, -1,5- and -1,6-phenylene, 2,5-dipropoxy-1,3-, -1,4- and -1,6-phenylene, 2,4,5-tripropoxy-1,3- and -1,6-phenylene, 2,4,6-tripropoxy-1,3-phenylene, 2-isopropoxy-1,3-, -1,4-, -1,5- and -1,6-phenylene, 2,3-diisopropoxy-1,4-, -1,5- and -1,6-phenylene, 2,4-diisopropoxy-1,3-, -1,5- and -1,6-phenylene, 2,5-diisopropoxy-1,3-, -1,4- and -1,6-phenylene, 2,4,5-triisopropoxy- 1,3- and -1,6-phenylene, 2,4,6-triisopropoxy-1,3-phenylene, 2-butoxy-1,3-, -1,4-, -1,5- and -1,6-phenylene, 2,3-dibutoxy-1,4-, -1,5- and -1,6-phenylene, 2,4-dibutoxy-1,3-, -1,5- and -1,6-phenylene, 2,5-dibutoxy-1,3-, -1,4- and -1,6-phenylene, 2,4,5-tributoxy-1,3- and -1,6-phenylene, 2,4,6-tributoxy-1,3-phenylene; 2-chloro-1,3-, -1,4-, -1,5- and -1,6-phenylene, 2,3-dichloro-1,4-, -1,5- and -1,6-phenylene, 2,4-dichloro-1,3-, -1,5- and -1,6-phenylene, 2,5-dichloro-1,3-, -1,4- and -1,6-phenylene; 2-hydroxy-1,3-, -1,4-, -1,5- and -1,6-phenylene, 2,3-dihydroxy-1,4-, -1,5- and -1,6-phenylene, 2,4-dihydroxy-1,3-, -1,5- and -1,6-phenylene, 2,5-dihydroxy-1,3-, -1,4- and -1,6-phenylene; 2-cyano-1,3-, -1,4-, -1,5- and -1,6-phenylene, 2,3-dicyano-1,4-, -1,5- and -1,6-phenylene, 2,4-dicyano-1,3-, -1,5- and -1,6-phenylene, 2,5-dicyano-1,3-, -1,4- and -1,6-phenylene;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl; 2-dioxanyl, 4-morpholinyl, 2- and 3-tetrahydrofuryl, 1-, 2- and 3-pyrrolidinyl and 1-, 2-, 3- and 4-piperidyl;

1,2- and 1,3-cyclopentylene, 1,3-, 1,4- and 1,5-(2-methyl)cyclopentylene, 1,3-, 1,4- and 1,5-(2-ethyl)cyclopentylene, 1,2-, 1,3- and 1,4-cyclohexylene, 1,3-, 1,4-, 1,5- and 1,6-(2-methyl)cyclohexylene, 1,3-, 1,4-, 1,5- and 1, 6-(2-ethyl)cyclohexylene, 1,3-, 1,4-, 1,5- and 1,6-(2-propyl) cyclohexylene, 1,3-, 1,4-, 1,5- and 1,6-(2-isopropyl)cyclohexylene, 1,3-, 1,4-, 1,5- and 1,6-(2-butyl)cyclohexylene, 1,3-, 1,4-, 1,5- and 1,6-(2-sec-butyl)cyclohexylene, 1,3-, 1,4-, 1,5- and 1,6-(2-tert-butyl)cyclohexylene, 1,2-, 1,3-, 1,4-cycloheptylene, 1,3-, 1,4-, 1,5-, 1,6- and 1,7-(2-methyl)cycloheptylene, 1,3-, 1,4-, 1,5-, 1,6- and 1,7-(2-ethyl)cycloheptylene, 1,3-, 1,4-, 1,5-, 1,6- and 1,7-(2-propyl)cycloheptylene, 1,3-, 1,4-, 1,5-, 1,6- and 1,7-(2-isopropyl)cycloheptylene, 1,3-, 1,4-, 1,5-, 1,6- and 1,7-(2-butyl)cycloheptylene, 1,3-, 1,4-, 1,5-, 1,6- and 1,7-(2-sec-butyl)cycloheptylene, 1,3-, 1,4-, 1,5-, 1,6- and 1,7-(2-tert-butyl)cycloheptylene, 1,2-, 1,3-, 1,4- and 1,5-cyclooctylene, 1,3-, 1,4-, 1,5-, 1,6-, 1,7- and 1,8-(2-methyl)cyclooctylene, 1,3-, 1,4-, 1,5-, 1,6-, 1,7- and 1,8-(2-ethyl)cyclooctylene, 1,3-, 1,4-, 1,5-, 1,6-, 1,7- and 1,8-(2-propyl)cyclooctylene; 2,3-, 2,5- and 2,6-(1,4-dioxanylene), 2,4- and 3,4-morpholinylene, 2,5- and 3,4-tetrahydrofurylene, 1,2-, 1,3-, 2,5- and 3,4-pyrrolidinylene and 1,2-, 1,3-, 1,4-, 2,3- and 2,6-piperidylene;

dimethylamino, diethylamino, dipropylamino, diisopropylamino, dibutylamino, diisobutylamino, di-tert-butylamino, dipentylamino, dihexylamino, diphenylamino, di-o-tolylamino, di-m-tolylamino, di-p-tolylamino, di(4-cyanophenyl)amino;

methylene-, ethylene-, propylene-, isopropylene-, butylene-, isobutylene-, sec-butylene- and tert-butylene-1,2-, -1,3- and -1,4-phenylene, methylene-, ethylene-, propylene-, isopropylene-, butylene-, isobutylene-, sec-butylene- and tert-butylene-1,3-, -1,4-, -1,5- and -1,6-(2-methyl)phenylene, methylene-, ethylene-, propylene-, isopropylene-, butylene-, isobutylene-, sec-butylene- and tert-butylene-1,4-, -1,5- and -1,6-(2,3-dimethyl)phenylene, ethylene-, ethylene-, propylene-, isopropylene-, butylene-, isobutylene-, sec-butylene- and tert-butylene-1,3-, -1,5- and -1,6-(2,4-dimethyl)phenylene, methylene-, ethylene-, propylene-, isopropylene-, butylene-, isobutylene-, sec-butylene- and tert-butylene-1,3-, -1,4- and -1,6-(2,5-dimethyl)phenylene, ethylene-, ethylene-, propylene-, isopropylene-, butylene-, isobutylene-, sec-butylene- and tert-butylene-1,3- and -1,6-(2,4,5-trimethyl)phenylene, methylene-, ethylene-, ropylene-, isopropylene-, butylene-, isobutylene-, sec-butylene- and tert-butylene-1,3-(2,4,6-trimethyl)phenylene, methylene-, ethylene-, propylene-, isopropylene-, butylene-, isobutylene-, sec-butylene- and tert-butylene-1,3-, -1,4-, -1,5- and -1,6-(2-ethyl)phenylene, methylene-, ethylene-, propylene-, isopropylene-, butylene-, isobutylene-, sec-butylene- and tert-butylene-1,4-, -1,5- and -1,6-(2,3-diethyl)phenylene, methylene-, ethylene-, propylene-, isopropylene-, butylene-, isobutylene-, sec-butylene- and tert-butylene-1,3-, -1,5- and -1,6-(2,4-diethyl)phenylene, methylene-, ethylene-, propylene-, isopropylene-, butylene-, isobutylene-, sec-butylene- and tert-butylene-1,3-, -1,4- and -1,6-(2,5-diethyl)phenylene, methylene-, ethylene-, propylene-, isopropylene-, butylene-, isobutylene-, sec-butylene- and tert-butylene-1,3- and -1,6-(2,4,5-triethyl)phenylene, methylene-, ethylene-, propylene-, isopropylene-, butylene-, isobutylene-, sec-butylene- and tert-butylene-1,3-(2,4,6-triethyl)phenylene, methylene-, ethylene-, propylene-, isopropylene-, butylene-, isobutylene-, sec-butylene- and tert-butylene-1,3-, -1,4-, -1,5- and -1,6-(2-propyl)phenylene, methylene-, ethylene-, propylene-, isopropylene-, butylene-, isobutylene-, sec-butylene- and tert-butylene-1,4-, -1,5- and -1,6-(2,3-dipropyl)phenylene, methylene-, ethylene-, propylene-, isopropylene-, butylene-, isobutylene-, sec-butylene- and tert-butylene-1,3-, -1,5- and -1,6-(2,4-dipropyl)phenylene, methylene-, ethylene-, propylene-, isopropylene-, butylene-, isobutylene-, sec-butylene- and tert-butylene-1,3-, -1,4- and -1,6-(2,5-dipropyl)phenylene, methylene-, ethylene-, propylene-, isopropylene-, butylene-, isobutylene-, sec-butylene- and tert-butylene-1,3- and -1,6-(2,4,5-tripropyl) phenylene, methylene-, ethylene-, propylene-, isopropylene-, butylene-, isobutylene-, sec-butylene- and tert-butylene-1,3-(2,4,6-tripropyl)phenylene, methylene-, ethylene-, propylene-, isopropylene-, butylene-, isobutylene-, sec-butylene- and tert-butylene-1,3-, -1,4-, -1,5- and -1,6-(2-isopropyl)phenylene, methylene-, ethylene-, propylene-, isopropylene-, butylene-, isobutylene-, sec-butylene- and tert-butylene-1,4-, -1,5- and -1,6-(2,3-diisopropyl)phenylene, methylene-, ethylene-, propylene-, isopropylene-, butylene-, isobutylene-, sec-butylene- and tert-butylene-1,3-, -1,5- and -1,6-(2,4-diisopropyl)phenylene, methylene-, ethylene-, propylene-, isopropylene-, butylene-, isobutylene-, sec-butylene- and and tert-butylene-1,3-, -1,4- and -1,6-(2,5-diisopropyl)phenylene, methylene-, ethylene-, propylene-, isopropylene-, butylene-, isobutylene-, sec-butylene- and tert-butylene-1,3- and -1,6-(2,4,5-triisopropyl)phenylene, methylene-, ethylene-, propylene-, isopropylene-, butylene-, isobutylene-, sec-butylene- and tert-butylene-1,3-(2,4,6-triisopropyl)phenylene, methylene-, ethylene-, propylene-, isopropylene-, butylene-, isobutylene-, sec-butylene- and tert-butylene-1,3-, -1,4-, -1,5- and -1,6-(2-butyl)phenylene, methylene-, ethylene-, propylene-, isopropylene-, butylene-, isobutylene-, sec-butylene- and tert-butylene-1,4-, -1,5- and -1,6-(2,3-dibutyl) phenylene, methylene-, ethylene-, propylene-, isopropylene-, butylene-, isobutylene-, sec-butylene- and tert-butylene-1,3-, -1,5- and -1,6-(2,4-dibutyl)phenylene, methylene-, ethylene-, propylene-, isopropylene-, butylene-, isobutylene-, sec-butylene- and tert-butylene-1,3-, -1,4- and -1,6-(2,5-dibutyl)phenylene, methylene-, ethylene-, propylene-, isopropylene-, butylene-, isobutylene-, sec-butylene- and tert-butylene-1,3- and -1,6-(2,4,5-tributyl)phenylene, methylene-, ethylene-, propylene-, isopropylene-, butylene-, isobutylene-, sec-butylene- and tert-butylene-1,3-(2,4,6-tributyl)phenylene, methylene-, ethylene-, propylene-, isopropylene-, butylene-, isobutylene-, sec-butylene- and tert-butylene-1,3-, -1,4-, -1,5- and -1,6-(2-isobutyl)phenylene, methylene-, ethylene-, propylene-, isopropylene-, butylene-, isobutylene-, sec-butylene- and tert-butylene-1,4-, -1,5- and -1,6-(2,3-diisobutyl) phenylene, methylene-, ethylene-, propylene-, isopropylene-, butylene-, isobutylene-, sec-butylene- and tert-butylene-1,3-, -1,5- and -1,6-(2,4-diisobutyl)phenylene, methylene-, ethylene-, propylene-, isopropylene-, butylene-, isobutylene-, sec-butylene- and tert-butylene-1,3-, -1,4- and -1,6-(2,5-diisobutyl)phenylene, methylene-, ethylene-, propylene-, isopropylene-, butylene-, isobutylene-, sec-butylene- and tert-butylene-1,3- and -1,6-(2,4,5-triisobutyl)phenylene, methylene-, ethylene-, propylene-, isopropylene-, butylene-, isobutylene-, sec-butylene- and tert-butylene-1,3-(2,4,6-triisobutyl)phenylene, methylene-, ethylene-, propylene-, isopropylene-, butylene-, isobutylene-, sec-butylene- and tert-butylene-1,3-, -1,4-, -1,5- and -1,6-(2-sec-butyl)phenylene, methylene-, ethylene-, propylene-, isopropylene-, butylene-, isobutylene-, sec-butylene- and tert-butylene-1,4-, -1,5- and -1,6-(2,3-di-sec-butyl)phenylene, methylene-, ethylene-, propylene-, isopropylene-, butylene-, isobutylene-, sec-butylene- and tert-butylene-1,3-, -1,5- and -1,6-(2,4-di-sec-butyl) phenylene, methylene-, ethylene-, propylene-, isopropylene-, butylene-, isobutylene-, sec-butylene- and tert-butylene-1,3-, -1,4- and -1,16-(2,5-di-sec-butyl)phenylene, methylene-, ethylene-, propylene-, isopropylene-, butylene-, isobutylene-, sec-butylene- and tert-butylene-1,3- and -1,6-(2,4,5-tri-sec-butyl)phenylene, methylene-, ethylene-, propylene-, isopropylene-, butylene-, isobutylene-, sec-butylene- and tert-butylene-1,3-(2,4,6-tri-sec-butyl)phenylene, methylene-, ethylene-, propylene-, isopropylene-, butylene-, isobutylene-, sec-butylene- and tert-butylene-1,3-, -1,4-, -1,5- and -1,6-(2-tert-butyl)phenylene, methylene-, ethylene-, propylene-, isopropylene-, butylene-, isobutylene-, sec-butylene- and tert-butylene-1,4-, -1,5- and -1,6-(2,3-di-tert-butyl)phenylene, methylene-, ethylene-, propylene-, isopropylene-, butylene-, isobutylene-, sec-butylene- and tert-butylene-1,3-, -1,5- and -1,6-(2,4-di-tert-butyl)phenylene, methylene-, ethylene-, propylene-, isopropylene-, butylene-, isobutylene-, sec-butylene- and tert-butylene-1,3-, -1,4- and -1,6-(2,5-di-tert-butyl)phenylene, methylene-, ethylene-, propylene-, isopropylene-, butylene-, isobutylene-, sec-butylene- and tert-butylene-1,3- and -1,6-(2,4,5-tri-tert-butyl)phenylene, methylene-, ethylene-, propylene-, isopropylene-, butylene-, isobutylene-, sec-butylene- and tert-butylene-1,3-(2,4,6-tri-tert-butyl)phenylene;

methylene-, ethylene-, propylene-, isopropylene-, butylene-, isobutylene-, sec-butylene- and tert-butylene-1,3-, -1,4-, -1,5- and -1,6-(2-methoxy)phenylene, methylene-, ethylene-, propylene-, isopropylene-, butylene-, isobutylene-, sec-butylene- and tert-butylene-1,4-, -1,5- and -1,6-(2,3-dimethoxy)phenylene, methylene-, ethylene-, propylene-, isopropylene-, butylene-, isobutylene-, sec-butylene- and tert-butylene-1,3-, -1,5- and -1,6-(2,4-dimethoxy)phenylene, methylene-, ethylene-, propylene-, isopropylene-, butylene-, isobutylene-, sec-butylene- and tert-butylene-1,3-, -1,4- and -1,6-(2,5-dimethoxy)phenylene, methylene-, ethylene-, propylene-, isopropylene-, butylene-, isobutylene-, sec-butylene- and tert-butylene-1,3- and -1,6-(2,4,5-trimethoxy)phenylene, methylene-, ethylene-, propylene-, isopropylene-, butylene-, isobutylene-, sec-butylene- and and tert-butylene-1,3-(2,4,6-trimethoxy)phenylene, methylene-, ethylene-, propylene-, isopropylene-, butylene-, isobutylene-, sec-butylene- and tert-butylene-1,3-, -1,4-, -1,5- and -1,6-(2-ethoxy) phenylene, methylene-, ethylene-, propylene-, isopropylene-, butylene-, isobutylene-, sec-butylene- and tert-butylene-1,4-, -1,5- and -1,6-(2,3-diethoxy)phenylene, methylene-, ethylene-, propylene-, isopropylene-, butylene-, isobutylene-, sec-butylene- and tert-butylene-1,3-, -1,5- and -1,6-(2,4-diethoxy)phenylene, methylene-, ethylene-, propylene-, isopropylene-, butylene-, isobutylene-, sec-butylene- and tert-butylene-1,3-, -1,4- and -1,6-(2,5-diethoxy)phenylene, methylene-, ethylene-, propylene-, isopropylene-, butylene-, isobutylene-, sec-butylene- and tert-butylene-1,3- and -1,6-(2,4,5-triethoxy)phenylene, methylene-, ethylene-, propylene-, isopropylene-, butylene-, isobutylene-, sec-butylene- and tert-butylene-1,3-(2,4,6-triethoxy)phenylene, methylene-, ethylene-, propylene-, isopropylene-, butylene-, isobutylene-, sec-butylene- and tert-butylene-1,3-, -1,4-, -1,5- and -1,6-(2-propoxy)phenylene, methylene-, ethylene-, propylene-, isopropylene-, butylene-, isobutylene-, sec-butylene- and tert-butylene-1,4-, -1,5- and -1,6-(2,3-dipropoxy)phenylene, methylene-, ethylene-, propylene-, isopropylene-, butylene-, isobutylene-, sec-butylene- and tert-butylene-1,3-, -1,5- and -1,6-(2,4-dipropoxy)phenylene, methylene-, ethylene-, propylene-, isopropylene-, butylene-, isobutylene-, sec-butylene- and tert-butylene-1,3-, -1,4- and -1,6-(2,5-dipropoxy)phenylene, methylene-, ethylene-, propylene-, isopropylene-, butylene-, isobutylene-, sec-butylene- and tert-butylene-1,3- and -1,6-(2,4,5-tripropoxy)phenylene, methylene-, ethylene-, propylene-, isopropylene-, butylene-, isobutylene-, sec-butylene- and tert-butylene-1,3-(2,4,6-tripropoxy)phenylene, methylene-, ethylene-, propylene-, isopropylene-, butylene-, isobutylene-, sec-butylene- and tert-butylene-1,3-, -1,4-, -1,5- and -1,6-(2-isopropoxy)phenylene, methylene-, ethylene-, propylene-, isopropylene-, butylene-, isobutylene-, sec-butylene- and tert-butylene-1,4-, -1,5- and -1,6-(2,3-diisopropoxy)phenylene, methylene-, ethylene-, propylene-, isopropylene-, butylene-, isobutylene-, sec-butylene- and tert-butylene-1,3-, -1,5- and -1,6-(2,4-diisopropoxy)phenylene, methylene-, ethylene-, propylene-, isopropylene-, butylene-, isobutylene-, sec-butylene- and tert-butylene-1,3-, -1,4- and -1,16-(2,5-diisopropoxy) phenylene, methylene-, ethylene-, propylene-, isopropylene-, butylene-, isobutylene-, sec-butylene- and tert-butylene-1,3- and -1,6-(2,4,5-triisopropoxy)phenylene, methylene-, ethylene-, propylene-, isopropylene-, butylene-, isobutylene-, sec-butylene- and tert-butylene-1,3-(2,4,6-triisopropoxy)phenylene, methylene-, ethylene-, propylene-, isopropylene-, butylene-, isobutylene-, sec-butylene- and tert-butylene-1,3-, -1,4-, -1,5- and -1,6-(2-butoxy)phenylene, methylene-, ethylene-, propylene-, isopropylene-, butylene-, isobutylene-, sec-butylene- and tert-butylene-1,4-, -1,5- and -1,6-(2,3-dibutoxy)phenylene, methylene-, ethylene-, propylene-, isopropylene-, butylene-, isobutylene-, sec-butylene- and tert-butylene-1,3-, -1,5- and -1,6-(2,4-dibutoxy)phenylene, methylene-, ethylene-, propylene-, isopropylene-, butylene-, isobutylene-, sec-butylene- and tert-butylene-1,3-, -1,4- and -1,6-(2,5-dibutoxy)phenylene, methylene-, ethylene-, propylene-, isopropylene-, butylene-, isobutylene-, sec-butylene- and tert-butylene-1,3- and -1,6-(2,4,5-tributoxy)phenylene, methylene-, ethylene-, propylene-, isopropylene-, butylene-, isobutylene-, sec-butylene- and tert-butylene-1,3-(2,4,6-tributoxy)phenylene;

ethylene-, ethylene-, propylene-, isopropylene-, butylene-, isobutylene-, sec-butylene- and tert-butylene-1,3-, -1,4-, -1,5- and -1,6-(2-cyano)phenylene, methylene-, ethylene-, propylene-, isopropylene-, butylene-, isobutylene-, sec-butylene- and tert-butylene-1,4-, -1,5- and -1,6-(2,3-dicyano)phenylene, ethylene-, ethylene-, propylene-, isopropylene-, butylene-, isobutylene-, sec-butylene- and tert-butylene-1,3-, -1,5- and -1,6-(2,4-dicyano)phenylene, methylene-, ethylene-, propylene-, isopropylene-, butylene-, isobutylene-, sec-butylene- and tert-butylene-1,3-, -1,4- and -1,6-(2,5-dicyano)phenylene;

methylene, ethylene-, propylene-, isopropylene-, butylene-, isobutylene-, sec-butylene- and tert-butylene-1,2-, -1,3-, -1,4-, -1,5-, -1,6-, -1,7-, -1,8-, -2,6- and -2,7-naphthylene, methylene, ethylene-, propylene-, isopropylene-, butylene-, isobutylene-, sec-butylene- and tert-butylene-2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- and -7,9-(1-methyl)naphthylene, methylene, ethylene-, propylene-, isopropylene-, butylene-, isobutylene-, sec-butylene- and tert-butylene-1,3-, -1,4-, -1,5-, -1,6-, -1,7-, -1,8-, -3,4-, -3,5-, -3,6-, -3,7-, -3,8-, -4,5-, -4,6-, -4,7-, -4,8-, -5,6-, -5,7-, -5,8-, -6,7-, -6,8- and -7,9-(2-methyl)naphthylene, methylene, ethylene-, propylene-, isopropylene-, butylene-, isobutylene-, sec-butylene- and tert-butylene-2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- and -7,9-(1-ethyl)naphthylene, methylene, ethylene-, propylene-, isopropylene-, butylene-, isobutylene-, sec-butylene- and tert-butylene-1,3-, -1,4-, -1,5-, -1,6-, -1,7-, -1,8-, -3,4-, -3,5-, -3,6-, -3,7-, -3,8-, -4,5-, -4,6-, -4,7-, -4,8-, -5,6-, -5,7-, -5,8-, -6,7-, -6,8- and -7,9-(2-ethyl)naphthylene, methylene, ethylene-, propylene-, isopropylene-, butylene-, isobutylene-, sec-butylene- and tert-butylene-2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- and -7,9-(1-propyl)naphthylene, methylene, ethylene-, propylene-, isopropylene-, butylene-, isobutylene-, sec-butylene- and tert-butylene-1,3-, -1,4-, -1,5-, -1,6-, -1,7-, -1,8-, -3,4-, -3,5-, -3,6-, -3,7-, -3,8-, -4,5-, -4,6-, -4,7-, -4,8-, -5,6-, -5,7-, -5,8-, -6,7-, -6,8- and -7,9-(2-propyl)naphthylene, methylene, ethylene-, propylene-, isopropylene-, butylene-, isobutylene-, sec-butylene- and tert-butylene-2,3-, -2,4-, -2,5-, -2,6-, -2,7-, -2,8-, -3,4-, -3,5-, -3,6-, -3,7-, -3,8-, -4,5-, -4,6-, -4,7-, -4,8-, -5,6-, -5,7-, -5,8-, -6,7-, -6,8- and -7,9-(1-isopropyl)naphthylene, methylene-, ethylene-, propylene-, isopropylene-, butylene-, isobutylene-, sec-butylene- and tert-butylene-1,3-, -1,4-, -1,5-, -1,6-, -1,7-, -1,8-, -3,4-, -3,5-, -3,6-, -3,7-, -3,8-, -4,5-, -4,6-, -4,7-, -4,8-, -5,6-, -5,7-, -5,8-, -6,7-, -6,8- and -7,9-(2-isopropyl)naphthylene;

methylene-, ethylene-, propylene-, isopropylene-, butylene-, isobutylene-, sec-butylene- and tert-butylene-2,3-, -2,4-, -2,5-, -2,6-, -3,4- and -3,5-pyridylene, methylene-, ethylene-, propylene-, isopropylene-, butylene-, isobutylene-, sec-butylene- and tert-butylene-3,4-, -3,5-, -3,6-, -4,5-, -4,6- and -5,6-(2-methyl)pyridylene, methylene-, ethylene-, propylene-, isopropylene-, butylene-, isobutylene-, sec-butylene- and tert-butylene-3,4-, -3,5-, -3,6-, -4,5-, -4,6- and -5,6-(2-ethyl)pyridylene, methylene-, ethylene-, propylene-, isopropylene-, butylene-, isobutylene-, sec-butylene- and tert-butylene-3,4-, -3,5-, -3,6-, -4,5-, -4,6- and -5,6-(2-propyl)pyridylene, methylene-, ethylene-, propylene-, isopropylene-, butylene-, isobutylene-, sec-butylene- and tert-butylene-3,4-, -3,5-, -3,6-, -4,5-, -4,6- and -5,6-(2-isopropyl)pyridylene, methylene-, ethylene-, propylene-, isopropylene-, butylene-, isobutylene-, sec-butylene- and tert-butylene-2,4-, -2,5-, -2,6-, -4,5-, -4,6- and -5,6-(3-methyl)pyridylene, methylene-, ethylene-, propylene-, isopropylene-, butylene-, isobutylene-, sec-butylene- and tert-butylene-2,4-, -2,5-, -2,6-, -4,5-, -4,6- and -5,6-(3-ethyl)pyridylene, methylene-, ethylene-, propylene-, isopropylene-, butylene-, isobutylene-, sec-butylene- and tert-butylene-2,4-, -2,5-, -2,6-, -4,5-, -4,6- and -5,6-(3-propyl)pyridylene, methylene-, ethylene-, propylene-, isopropylene-, butylene-, isobutylene-, sec-butylene- and tert-butylene-2,4-, -2,5-, -2,6-, -4,5-, -4,6- and -5,6-(3-isopropyl)pyridylene, methylene-, ethylene-, propylene-, isopropylene-, butylene-, isobutylene-, sec-butylene- and tert-butylene-2,3-, -2,5-, -2,6-, -3,5-, -3,6- and -5,6-(4-methyl)pyridylene, methylene-, ethylene-, propylene-, isopropylene-, butylene-, isobutylene-, sec-butylene- and tert-butylene-2,3-, -2,5-, -2,6-, -3,5-, -3,6- and -5,6-(4-ethyl)pyridylene, methylene-, ethylene-, propylene-, isopropylene-, butylene-, isobutylene-, sec-butylene- and tert-butylene-2,3-, -2,5-, -2,6-, -3,5-, -3,6- and -5,6-(4-propyl)pyridylene, methylene-, ethylene-, propylene-, isopropylene-, butylene-, isobutylene-, sec-butylene- and tert-butylene-2,3-, -2,5-, -2,6-, -3,5-, -3,6- and -5,6-(4-isopropyl)pyridylene;

methylene-, ethylene-, propylene-, isopropylene-, butylene-, isobutylene-, sec-butylene- and tert-butylene-2,5- and 3,4-pyrrylene, methylene-, ethylene-, propylene-, isopropylene-, butylene-, isobutylene-, sec-butylene- and tert-butylene-2,4- and 2,5-pyrimidylene, methylene-, ethylene-, propylene-, isopropylene-, butylene-, isobutylene-, sec-butylene- and tert-butylene-2,3-, 2,5- and 2,6-pyrazylene, methylene-, ethylene-, propylene-, isopropylene-, butylene-, isobutylene-, sec-butylene- and tert-butylene-3,5-pyrazolylene, methylene-, ethylene-, propylene-, isopropylene-, butylene-, isobutylene-, sec-butylene- and tert-butylene-1,2-, 1,4-, 1,5-, 2,4- and 2,5-imidazolylene, methylene-, ethylene-, propylene-, isopropylene-, butylene-, isobutylene-, sec-butylene- and tert-butylene-2,4- and 2,5-thiazolylene, methylene-, ethylene-, propylene-, isopropylene-, butylene-, isobutylene-, sec-butylene- and tert-butylene-3,5- and 3,6-(1,2,4-triazylene), methylene-, ethylene-, propylene-, isopropylene-, butylene-, isobutylene-, sec-butylene- and tert-butylene-2,4-(1,3,5-triazylene), methylene-, ethylene-, propylene-, isopropylene-, butylene-, isobutylene-, sec-butylene-. and tert-butylene-3,5-, 3,6-, 3,8- and 5,8-quinaldylene, methylene-, ethylene-, propylene-, isopropylene-, butylene-, isobutylene-, sec-butylene- and tert-butylene-3,5-, 3,6-, 3,8- and 5,8-quinolinylene, methylene-, ethylene-, propylene-, isopropylene-, butylene-, isobutylene-, sec-butylene- and tert-butylene-2,4- and 2,5-benezimidazolylene and methylene-, ethylene-, propylene-, isopropylene-, butylene-, isobutylene-, sec-butylene- and tert-butylene-1,3-, 1,4-, 1,5- and 1,6-isoquinolylene.

Examples of the group P capable of free-radical polymerization of the general formula II are in particular vinyl, allyl, methallyl, acrylamido, methacrylamido, acryloxy, methacryloxy, 3-vinylureido, 3-allylureido, 3-methallylureido, N-vinylaminocarbonyloxy, N-allylaminocarbonyloxy and N-methallylaminocarbonyloxy.

The 9-cyano-substituted perylene-3,4-dicarboxylic monoimides I can advantageously be prepared by the three processes according to the invention, starting from the perylene-3,4-dicarboxylic anhydride known from the literature or the 9-bromoperylene-3,4-dicarboximides of the formula VI described in WO-A-96/22331 and WO-A-01/16109.

To prepare the non- or monofunctional 9-cyanoperylene-3,4-dicarboxylic monoimides Ia according to the invention, perylene-3,4-dicarboxylic anhydride is initially selectively brominated in the 9-position with elemental bromine in a step a), the 9-bromoperylene-3,4-dicarboxylic anhydride IIIa obtained in step a) is reacted with copper(I) cyanide in excess in a step b), and, in a final step c), the 9-cyanoperylene-3,4- dicarboxylic anhydride IIIa obtained in step b) is reacted with a primary amine IV to give the desired 9-cyanoperylene-3,4-dicarboxylic monoimides Ia.

Step a) of the preparative process according to the invention, the reaction of perylene-3,4-dicarboxylic anhydride with elemental bromine, is carried out in the presence of concentrated sulfuric acid or of an aliphatic monocarboxylic acid as a solvent.

Examples of suitable aliphatic monocarboxylic acids are in particular carboxylic acids having from 2 to 6 carbon atoms, specifically acetic acid, propionic acid, butyric acid, pentane carboxylic acid and hexanecarboxylic acid, and also mixtures thereof.

Typically from 10 to 50 g, preferably from 15 to 30 g, of solvent are used per gram of perylene-3,4-dicarboxylic anhydride to be brominated.

In general, the presence of a halogenation catalyst is not necessary. However, if acceleration of the bromination reaction is required (by a factor of about 2 to 5), it is advisable to add elemental iodine, preferably in an amount of from 1 to 5 mol %, based on petylene-3,4-dicarboxylic anhydride.

In general, the molar ratio of bromine to perylene-3,4-dicarboxylic anhydride is from about 0.8:1 to 2:1, preferably from 1.0:1 to 1.5:1.

The reaction temperature is generally from 0 to 70° C., in particular from 0 to 10° C. when conc. sulfuric acid is used, and from 20 to 60° C. when aliphatic carboxylic acids are used, as solvents.

Depending on the reaction temperature and the presence or absence or iodine, the bromination is typically complete within from 2 to 12 h.

In terms of method, the procedure in step a) is advantageously as follows:

Solvent and perylene-3,4-dicarboxylic anhydride are initially charged, any catalyst is added and the desired amount of bromine is then added within from 5 to 10 min, the mixture is brought to the desired reaction temperature with stirring, stirred at reaction temperature for a further 2 to 12 h and excess bromine is removed with a vigorous nitrogen stream. When sulfuric acid is used, the reaction mixture is introduced into ten times the volume of ice-water, and the precipitated product is filtered off, washed with water until the filtrate is neutral and dried under reduced pressure at about 120° C. When aliphatic monocarboxylic acids are used as the solvent, the reaction mixture is cooled to room temperature, optionally diluted with double the volume of an aliphatic alcohol such as methanol, and the precipitated solid is filtered off, stirred successively in methanol and 2% by weight sodium thiosulfate solution, filtered off again, washed with hot water until the filtrate is neutral and salt-free and dried at 120° C. under reduced pressure. The purity of the 9-bromoperylenedicarboxylic anhydride IIIa prepared in this way and likewise according to the invention is generally >97% and is therefore generally sufficient for further processing. If desired, a purification can be carried out by column filtration on silica gel using methylene chloride as the eluent or by extraction with a solvent such as methanol.

In step b) of the process according to the invention, the 9-bromoperylene-3,4-dicarboxylic anhydride IIIa obtained in step a) is reacted with copper(I) cyanide in excess in a high-boiling inert diluent, optionally with the addition of a basic nitrogen compound or of a nitrogen heterocycle as a catalyst.

Suitable high-boiling inert diluents for this purpose are in particular (bi)cycloaliphatics such as cyclohexane and its alkylated derivatives, and also decahydronaphthalene, cyclic sulfoxides such as sulfolane, and polar solvents, in particular nitrogen heterocycles such as pyridine, pyrimidine, quinoline, isoquinoline, quinaldine and N-methylpyrrolidone, and also carboxamides such as N,N-dimethylformamide and N,N-dimethylacetamide, and preference is given to sulfolane, N-methylpyrrolidone and N,N-dimethylacetamide. The last two classes of compound may also simultaneously serve as the catalyst.

Typically from 10 to 50 g, preferably from 10 to 25 g, of diluent are used per gram of 9-bromoperylene-3,4-dicarboxylic anhydride IIIa.

When (bi)cycloaliphatics are used as the high-boiling, inert diluent, the substitution reaction can be distinctly accelerated by adding from 5 to 10% by volume of a basic nitrogen compound or of a nitrogen heterocycle as a catalyst; in all other cases, there is no need for such an addition.

In general, from 1 to 3 mol, preferably from 1.5 to 2.5 mol, of copper(I) cyanide are used per mole of bromine atom to be substituted.

The reaction temperature is generally from 150 to 350° C., in particular from 180 to 300° C.

Depending on the reaction temperature, the substitution reaction is typically complete within from 0.5 to 6 h.

In terms of method, the procedure in step b) is advantageously as follows:

A mixture of 9-bromoperylene-3,4-dicarboxylic anhydride IIIa, copper(I) cyanide, diluent and optionally basic nitrogen catalyst is heated to the desired reaction temperature with stirring in a nitrogen atmosphere for from 0.5 to 6 h. After the reaction mixture is cooled, it is diluted with twice to three times the volume of an aliphatic alcohol such as methanol or else an alcohol/water mixture, and the precipitated solid is filtered off, stirred in an iron(III) chloride solution in hydrochloric acid to destroy excess copper(I) cyanide and filtered again, and the residue is washed with hot water until the filtrate is neutral and virtually colorless, and dried at 120° C. under reduced pressure.

The purity of the 9-cyanoperylenedicarboxylic anhydride IIIb prepared in this way and likewise according to the invention is typically >95% and is therefore generally sufficient for further processing. If desired, in a similar manner to the 9-bromoperylenedicarboxylic anhydride IIIa, a purification can be carried out by column filtration on silica gel using methylene chloride as the eluent or by extraction with a solvent such as methanol.

Step c) of the preparative process according to the invention, the reaction of the 9-cyanoperylene-3,4-dicarboxylic anhydride IIIb obtained in step b) with the primary amine IV to give the desired 9-cyanoperylene-3,4-dicarboxylic monoimides Ia, is effected in water or a suitable inert organic solvent, optionally with the addition of an imidation catalyst.

Depending on the solubility behavior, the polarity and the reactivity of the primary amine IV used, either water or else inert organic solvent are used. Short-chain, aliphatic and cycloaliphatic amines having high reactivity can advantageously be converted in water as the solvent, while long-chain aliphatic and aromatic amines of moderate and low reactivity and limited water solubility require the use of more or less polar, inert organic solvents.

Suitable inert organic solvents are aromatics such as toluene and xylene (all isomers), (bi)cycloaliphatics such as alkyl-substituted cyclohexane and decahydronaphthalene, and also especially polar basic nitrogen compounds, in particular nitrogen heterocycles such as pyridine, pyrimidine, quinoline, isoquinoline, quinaldine and N-methylpyrrolidone, and also carboxamides such as N,N-dimethylformamide and N,N-dimethylacetamide, and preference is given to N-methylpyrrolidone.

The amount of solvent is in itself not critical, although typically from 10 to 100 g, preferably from 20 to 50 g, of solvent are used per gram of IIIb.

For the reaction of relatively unreactive, in particular sterically hindered primary amines, the addition of an imidation catalyst is necessary.

Suitable imidation catalysts are organic and inorganic salts of transition metals such as zinc, iron and copper, and of magnesium, for example zinc acetate, zinc propionate, zinc oxide, iron(II) acetate, iron(III) chloride, iron(II) sulfate, copper(II) acetate, copper(I) oxide, copper(II) oxide and magnesium acetate. It will be appreciated that mixtures of the catalysts mentioned can also be used.

In general, from 5 to 40% by weight, preferably from 5 to 15% by weight, of catalyst is used, based on IIIb.

Useful primary amines IV in the preparative process according to the invention are all amines stable under the reaction conditions which form imides with perylene-3,4-dicarboxylic anhydrides.

Typically, the molar ratio of amine IV to IIIb, depending on the reactivity of the amine, is from 0.8:1 to 5:1.

The reaction temperature in step c) is generally from 40 to 250° C. When nonfunctional, short-chain aliphatic or cycloaliphatic amines of high reactivity are reacted, preference is given to temperatures of from 40 to 100° C., and when non- and monofunctional aliphatic or alkylaromatic amines of moderate to high reactivity are reacted, preference is given to temperatures of from 120 to 200° C., and when relatively unreactive, non- and monofunctional aromatic amines are reacted, preference is given to temperatures of from 180 to 250° C.

It is advisable to work with the use of a protective gas atmosphere (for example nitrogen).

Step c) of the process according to the invention can be carried out at atmospheric pressure or at an elevated pressure of typically up to 10 bar. The method under pressure is advantageous in particular when volatile amines are used (boiling point ≦ about 180° C.).

Typically, the reaction is complete within from 1 to 10 h, in particular within from 1 to 5 h.

In terms of method, the procedure in step c) is advantageously as follows:

The amine IV, solvent and optionally catalyst are initially charged, the 9-cyanoperylene-3,4-dicarboxylic anhydride IIIb is added in portions at room temperature, the apparatus is purged with nitrogen for about 15 min, and the mixture is heated to the reaction temperature with stirring and kept at this temperature for from about 1 to 5 h. After cooling to room temperature, half of the solvent is optionally removed under reduced pressure, and the precipitated reaction product is filtered off, washed with an aliphatic alcohol such as methanol and dried.

If the reaction is to be carried out under pressure, the reaction vessel used is a pressure apparatus to which a nitrogen pressure of from about 1 to 2 bar is applied after charging with the components, and it is subsequently heated to the reaction temperature for the desired time under the autogenous pressure developing and decompressed after cooling.

The purity of the 9-cyanoperylene-3,4-dicarboxamides Ia prepared in this way and according to the invention is generally >98% and is therefore sufficient for further processing. If desired, a further purification can be carried out by column filtration on silica gel using a halogenated hydrocarbon such as methylene chloride, chloroform or tetrachloroethane as the eluent or by a clarifying filtration of a hot solution of the imide Ia in N-methylpyrrolidone (NMP) and subsequent precipitation of the product of value by adding an aqueous aliphatic alcohol such as methanol or ethanol.

To prepare the 9-cyanoperylene-3,4-dicarboxylic monoimides Ib containing a group P capable of free radical polymerization and likewise according to the invention, in a further step similar to the procedure described in WO-A-99/40123, monofunctional 9-cyanoperylenedicarboxylic monoimides of the formula Ia where Y' is amino or hydroxyl are reacted with the carbonyl chlorides V in an inert aprotic diluent, with the addition of a nitrogen base.

Suitable inert aprotic diluents are aliphatic and cycloaliphatic ethers such as diethyl ether, dipropyl ether and dibutyl ether, dimethoxyethane and diethoxyethane, and also tetrahydrofuran and dioxane, aromatics such as toluene or xylene (all isomers), (bi)cycloaliphatics such as alkyl-substituted cyclohexane and decahydronaphthalene, and also especially polar basic nitrogen compounds, in particular nitrogen heterocycles such as quinoline, isoquinoline, quinaldine and N-methylpyrrolidone, and also carboxamides such as N,N-dimethylformamide and N,N-dimethylacetamide, and preference is given to dioxane and N,N-dimethylformamide.

Preference is given to carrying out the reaction of the acid chlorides V in the presence of at least equimolar amounts of a nitrogen base which may also serve as a cosolvent. Preferred nitrogen bases are trialkylamines such as triethylamine, tripropylamine and tributylamine, sterically hindered bicycles such as diazabicyclooctane, diazabicyclononene (DBN) and diazabicycloundecene (DBU), and nitrogen heterocycles such as pyridine and pyrimidine, and preference is given to DBU and pyridine.

Typically, the molar ratio of carbonyl chloride V to 9-cyanoperylenedicarboxylic monoimide Ia, depending on the reactivity of the 9-cyanoperylene-3,4-dicarboxylic imide Ia, is from 1:1 to 5:1.

The reaction temperature is typically from 20 to 150° C., depending on the reactivity of the 9-cyanoperylene-3,4-dicarboxylic imide Ia and on the polymerization tendency of the desired end product Ib. For example, in the case of the reaction of hydroxy-functional 9-cyanoperylenedicarboxylic monoimides Ia with acrylic chlorides, it is preferably from 20 to 70° C., whereas preference is given to temperatures of from 40 to 90° C. for the reaction with methacrylic chlorides.

Typically, the reaction is complete within from 1 to 5 h, in particular within from 1 to 2 h.

In terms of method, the procedure is advantageously as follows:

A solution or dispersion of the monofunctional 9-cyanoperylenedicarboxylic monoimide Ia is initially charged in the diluent or optionally the nitrogen base and heated to the desired reaction temperature, a solution of the acid chloride V in the diluent is slowly added dropwise and the mixture is stirred at this temperature for from 1 to 2 h. After the distillative removal of diluent and excess nitrogen base under reduced pressure, the residue is dissolved in chloroform and subjected to a column filtration using silica gel as the stationary phase. Finally, the solvent is removed under reduced pressure.

The purity of the 9-cyanoperylenedicarboxylic imides Ib prepared in this way and according to the invention is generally >98% and is therefore sufficient for further processing.

To prepare the nonfunctional 9-cyanoperylenedicarboxylic monoimides Ic likewise according to the invention, a 9-bromoperylene-3,4-dicarboxylic monoimide VI prepared by the processes described in WO-A-96/22331 and WO-A-01/16109 is converted to the desired 9-cyanoperylene-3,4-dicarboxylic monoimide Ic by reaction with copper(I) cyanide without a diluent or in a high-boiling inert diluent, optionally with the addition of a basic nitrogen compound or of a nitrogen heterocycle as a catalyst.

Suitable high-boiling, inert diluents for this purpose are in particular (bi)cycloaliphatics such as cyclohexane and its alkylated derivatives and also decahydronaphthalene, cyclic sulfoxides such as sulfolane, and polar solvents, in particular nitrogen heterocycles such as pyridine, pyrimidine, quinoline, isoquinoline, quinaldine and N-methylpyrrolidone, and also carboxamides such as N,N-dimethylformamide and N,N-dimethylacetamide, and preference is given to sulfolane, N-methylpyrrolidone and N,N-dimethylacetamide. The last two classes of compound may also serve simultaneously as the catalyst.

Typically from 5 to 30 g, preferably from 5 to 15 g, of diluent are used per gram of 9-bromoperylene-3,4-dicarboxylic monoimide VI.

In the case of reaction without diluent, it is absolutely necessary to add from 20 to 30% by weight of a basic nitrogen compound or of a nitrogen heterocycle as a catalyst to carry out the reaction. In the case of the use of (bi)cycloaliphatics as the high-boiling inert diluent also, the substitution reaction can be distinctly accelerated by adding from 5 to 10% by volume of a basic nitrogen compound or of a nitrogen heterocycle as a catalyst; in all other cases there is no need for such an addition.

In general, from 1 to 3 mol, preferably from 1.2 to 2.0 mol, of copper(I) cyanide are used per mole of bromine to be substituted.

The reaction temperature is generally from 150 to 350° C., in particular from 180 to 300° C.

Depending on the reaction temperature, the substitution reaction is typically complete within from 0.5 to 4 h.

In terms of method, the procedure is advantageously as follows:

A mixture of 9-bromoperylene-3,4-dicarboxylic monoimide VI, copper(I) cyanide, diluent and optionally basic nitrogen catalyst is heated to the desired reaction temperature with stirring in a nitrogen atmosphere for from 0.5 to 4 h. After, the reaction mixture is cooled, it is diluted with from the same to double the volume of an aliphatic alcohol such as methanol or else an alcohol/water mixture, and the precipitated solid is filtered off, stirred in an iron(III) chloride solution in hydrochloric acid to destroy excess copper(I) cyanide and filtered again, and the residue is washed with hot water until the filtrate is neutral and virtually colorless, and dried at 120° C. under reduced pressure.

For purification, the crude product prepared in this way is dissolved in N-methylpyrrolidone (NMP) at from 70 to 100° C., admixed with activated carbon, stirred for a further 30 min and hot-filtered. After cooling to 60° C., the product is precipitated by adding from 60 to 65% by volume ethanol, stirred at 60° C. for a further 3 h, slowly cooled to room temperature, filtered off, washed with ethanol to free it of NMP and dried.

In general, the 9-cyanoperylenedicarboxylic monoimides obtained according to the invention already have such a high purity (>98%) that further purification may be dispensed with. Analytically pure products can be prepared by recrystallization from aromatic solvents such as toluene and xylene, or halogenated hydrocarbons such as methylene chloride and chloroform, or by filtration of a solution of the products in these solvents through silica gel and subsequent concentration.

With the aid of the preparative process according to the invention, the 9-cyano-substituted perylene-3,4-dicarboxylic monoimides I can be obtained in high purities (generally >98%) and good yields in a manner which is simple and economical in terms of method.

The 9-cyano-substituted perylene-3,4-dicarboxylic monoimides of the formulae Ia and Ic according to the invention are advantageously suitable as fluorescent dyes, for coloring high molecular weight organic and inorganic materials, in particular plastics, paints, printing inks, inorganic-organic composites and oxidic layer systems, as dispersants, pigment additives for organic pigments and intermediates for the preparation of fluorescent dyes and pigment additives, for producing aqueous polymer dispersions and inkjet inks absorbing and/or emitting in the yellow region of the electromagnetic spectrum, as photoconductors in electrophotography, as coloring or color-correcting components in emissive and transflective color filters and in retroreflective components, as emitters in electroluminescence and chemiluminescence applications, as active components in fluorescence conversion, in fluorescence solar collectors, in bioluminescence arrays and also in photovoltaics and as laser dyes.

The 9-cyanosubstituted perylene-3,4-dicarboxylic monoimides of the formula Ib which are likewise according to the invention are suitable in particular as fluorescent dyes, for reactive coloration of high molecular weight organic and inorganic materials, in particular of paints, printing inks and inorganic-organic composites, for producing bleeding-resistant aqueous polymer dispersions which absorb and/or emit in the yellow region of the electromagnetic spectrum, as coloring or color-correcting components in emissive and transreflective color filters and in retroreflective components, and also as migration-stable emitters in electroluminescence and chemiluminescence applications.

EXAMPLES a) Preparation of 9-bromoperylene-3,4-dicarboxylic anhydride IIIa

Example 1

10 g (30 mmol) of perylene-3,4-dicarboxylic anhydride were dissolved in 200 g of sulfuric acid with stirring at 0-10° C., and then admixed initially with 0.2 g of iodine as the catalyst and subsequently with 5 g (30 mmol) of bromine within 10 min. After stirring at this temperature for 4 hours and expelling excess bromine with nitrogen, the reaction mixture was precipitated in 1000 ml of ice-water. The precipitated product was filtered off, washed with water until the filtrate was neutral and dried under reduced pressure at 120° C.

12.0 g of 9-bromoperylene-3,4-dicarboxylic anhydride IIIa were obtained in the form of a red-brown, amorphous solid having a melting point of >300° C., which corresponds to a yield of 96%.

Analytical Data:
Elemental analysis (% by weight calc./found): C: 65.85/65.7; H: 2.25/2.25; O: 11.95/12.2; Br: 19.95/19.85;
Mass (FD, 8 kV): m/z=400.4 [M$^+$, 100%];
IR (KBr): ν=1750 (s, C=O), 1725 (s, C=O) cm$^{-1}$;
UV/VIS (CHCl$_3$): λ$_{max}$ (ε)=487 (9750), 511 (31330) nm.

Example 2

A mixture of 10 g (30 mmol) of perylene-3,4-dicarboxylic anhydride, 0.2 g of iodine as a catalyst, 7.5 g (45 mmol) of bromine (added dropwise within 10 min) and 250 ml of glacial acetic acid was heated to 50° C. with stirring for 8 h. After cooling of the reaction solution to room temperature and expulsion of excess bromine with nitrogen, the reaction mixture was diluted with 500 ml of methanol. The precipitated solid was filtered off, slurried in 150 ml of methanol, stirred at room temperature for 1 h, filtered off, stirred in 500 ml of 2% by weight sodium thiosulfate solution for 2 h, filtered off, washed with water at 70° C. until the filtrate was neutral and almost colorless and dried at 120° C. under reduced pressure.

11.3 g of 9-bromoperylene-3,4-dicarboxylic anhydride IIIa were obtained in the form of a red-brown amorphous solid having a melting point of >300° C., which corresponds to a yield of 94%.

b) Preparation of 9-cyanoperylene-3,4-dicarboxylic anhydride IIIb

Examples 3 to 5

A mixture of 10 g (25 mmol) of 9-bromoperylene-3,4-dicarboxylic anhydride IIIa, 4.5 g (50 mmol) of copper(I) cyanide and 120 ml of the diluent D was heated to T° C. with stirring in a nitrogen atmosphere for t h. After the reaction mixture was cooled to 60° C. (Example 3) or room temperature (Examples 4 and 5), it was diluted with 300 ml of methanol (Example 3) or a mixture of methanol and water in a volume ratio of 1:3 (Examples 4 and 5). The precipitated solid was filtered off, introduced into a mixture of 25 g of iron(III) chloride hexahydrate, 100 ml of water and 20 ml of conc. hydrochloric acid, the resulting suspension was stirred first at room temperature for 2 h and then at 70° C. for 1 h, filtered again, and the residue was washed with warm water at 70° C. until the filtrate was neutral and almost colorless, and dried at 120° C. under reduced pressure.

Further details on these experiments and also their results are compiled in Table 1.

TABLE 1

| Ex. | Diluent D | t [h] | T [° C.] | Yield/Purity [g (%)]/[%] | Appearance |
|---|---|---|---|---|---|
| 3 | Sulfolane | 1 | 280 | 7.5 (86)/>97 | brown, microcrystalline |
| 4 | N-Methyl-pyrrolidone | 3 | 200 | 7.65 (88)/>95 | brown, amorphous |
| 5 | N,N-Dimethyl-acetamide | 6 | 165 | 7.4 (85)/>95 | brown, amorphous |

Analytical Data:
Melting point : >300° C.;
Elemental analysis (% by weight calc./found): C, 79.55/79.2; H, 2.6/2.6; N, 4.05/4.1; O, 13.8/14.1.
Mass (FD, 8 kV): m/z=347.2 [M$^+$, 100%];
IR (KBr): ν=2200 (m, C≡N), 1760 (s, C=O), 1725 (s, C=O) cm$^{-1}$;
UV/VIS (CHCl$_3$): λ$_{max}$ (ε)=473 (14870), 496 (39750) nm.

c) Preparation of the 9-cyanoperylene-3,4-dicarboxylic imides Ia

Examples 6 to 16 x g (X mmol) of amine IV and y g (Y mmol) of catalyst C were initially charged with stirring in v ml of solvent S and admixed in portions at room temperature with 6.95 g (20 mmol) of 9-cyanoperylene-3,4-dicarboxylic anhydride IIIb. After the apparatus was purged with nitrogen for 15 minutes, the mixture was heated with stirring to the reaction temperature T° C. for t h. After cooling to room temperature, the precipitated reaction product, either directly (Examples 6, 12, 14-16) or else after removal of half of the solvent under reduced pressure (Examples 7-11, 13) was filtered off, washed with a lot of methanol and dried at 100° C. under reduced pressure.

Further details on these experiments and also their results are compiled in Table 2.

In the table:

TABLE 2

| Ex. | Amine IV | x [g] | X [mmol] | Cat. C | y [g] | Y [mmol] | L | v [ml] | t [h] | Yield [g/%] | Appearance | m.p. [° C.] |
|---|---|---|---|---|---|---|---|---|---|---|---|---|
| 6 | Methylamine | 0.9 | 30 | — | — | — | H$_2$O | 300 | 5 | 6.2/86 | red-brown, crystalline | >300 |
| 7 | n-Dodecylamine | 4.1 | 22 | — | — | — | DMAc | 100 | 1.5 | 9.1/88 | red-brown, amorphous | 219-221 |
| 8 | 5-Nonylamine | 3.6 | 25 | — | — | — | NMP | 150 | 2 | 7.5/79 | red-orange, amorphous | 203-204 |
| 9 | 2,6-Diisopropylaniline | 7.1 | 40 | ZnAc | 1.0 | 4.5 | NMP | 200 | 3 | 8.6/85 | orange-red, microcrystalline | >300 |
| 10 | 2,5-Di-tertbutylaniline | 8.2 | 40 | ZnAc | 1.0 | 4.5 | NMP | 200 | 3 | 9.3/87 | orange, microcrystalline | >300 |
| 11 | p-Methoxybenzylamine | 3.45 | 25 | — | — | — | NMP | 200 | 2 | 7.65/82 | brown-orange, amorphous | >300 |
| 12 | 5-Amino-1-pentanol | 2.3 | 22 | — | — | — | NMP | 200 | 1.5 | 6.85/79 | brown-red, microcrystalline | 282-284 |
| 13 | Hexamethylene diamine | 11.6 | 100 | — | — | — | NMP | 200 | 3 | 6.7/75 | brown, amorphous | 273-275 |
| 14 | 2-(p-Amino phenyl)ethanol | 5.5 | 40 | Cu$_2$O | 0.5 | 3.5 | NMP | 350 | 3 | 6.35/68 | red-orange, microcrystalline | >300 |
| 15 | p-Hydroxyphenethylamine | 3.45 | 25 | — | — | — | NMP | 250 | 3 | 7.5/80 | brown-orange, amorphous | >300 |
| 16 | p-Aminobenzene sulfonic acid | 17.3 | 100 | Cu$_2$O | 1.0 | 7.0 | NMP | 350 | 5 | 6.55/65 | red-brown, crystalline | >300 |

ZnAc: Zinc acetate dihydrate
DMAc: N,N-Dimethylacetamide
NMP: N-Methylpyrrolidone Analytical Data on Example 6:
Elemental analysis (% by weight calc./found): C: 80.0/79.9; H: 3.35/3.3; N: 7.75/7.8; O: 8.9/9.0;
Mass (FD, 8 kV): m/z=360.2 [M+, 100%];
IR (KBr): ν=2198 (m, C≡N), 1679 (s, C=O), 1648 (s, C=O) cm$^{-1}$;
UV/VIS (CHCl$_3$): $\lambda_{max}$ (ε)=471 (40110), 500 (52300) nm.

Analytical Data on Example 7:
Elemental analysis (% by weight calc./found): C: 81.7/81.5; H: 6.65/6.7; N: 5.45/5.5; O: 6.2/6.3;
Mass (FD, 8 kV): m/z=514.4 [M+, 100%];
IR (KBr): ν=2200 (m, C≡N), 1680 (s, C=O), 1649 (s, C=O) cm$^{-1}$;
UV/VIS (CHCl$_3$): $\lambda_{max}$ (ε)=472 (37340), 501 (48060) nm.

Analytical Data on Example 8:
Elemental analysis (% by weight calc./found): C: 81.35/81.3; H: 5.95/5.9; N: 5.95/6.0; O: 6.75/6.8;
Mass (FD, 8 kV): m/z=472.5 [M+, 100%];
IR (KBr): ν=2199 (m, C≡N), 1681 (s, C=O), 1648 (s, C=O) cm$^{-1}$;
UV/VIS (CHCl$_3$): $\lambda_{max}$ (ε)=473 (37860), 502 (50120) nm.

Analytical Data on Example 9:
Elemental analysis (% by weight calc./found): C: 83.0/83.2; H: 5.15/5.1; N: 5.55/5.5; O: 6.3/6.2;
Mass (FD, 8 kV): m/z=506.4 [M+, 100%];
IR (KBr): ν=2202 (m, C≡N), 1682 (s, C=O), 1651 (s, C=O) cm$^{-1}$;
UV/VIS (CHCl$_3$): $\lambda_{max}$ (ε)=474 (36420), 504 (45550) nm.

Analytical Data on Example 10:
Elemental analysis (% by weight calc./found): C: 83.1/83.2; H: 5.65/5.6; N: 5.25/5.2; O: 6.0/6.0;
Mass (FD, 8 kV): m/z=534.4 [M+, 100%];
IR (KBr): ν=2200 (m, C≡N), 1683 (s, C=O), 1652 (s, C=O) cm$^{-1}$;
UV/VIS (CHCl$_3$): $\lambda_{max}$ (ε)=473 (35040), 505 (42990) nm.

Analytical Data on Example 11:
Elemental analysis (% by weight calc./found): C: 79.8/79.8; H: 3.9/3.9; N: 6.0/6.0; O: 10.3/10.3;
Mass (FD, 8 kV): m/z=466.3 [M+, 100%];
IR (KBr): ν=2200 (m, C≡N), 1680 (s, C=O), 1650 (s, C=O) cm$^{-1}$;
UV/VIS (CHCl$_3$): $\lambda_{max}$ (ε)=472 (37080), 502 (47660) nm.

Analytical Data on Example 12:
Elemental analysis (% by weight calc./found): C: 77.75/77.6; H: 4.65/4.7; N: 6.5/6.5; O: 11.1/11.2;
Mass (FD, 8 kV): m/z=432.4 [M+, 100%];
IR (KBr): ν=2200 (m, C≡N), 1680 (s, C=O), 1650 (s, C=O) cm$^{-1}$;
UV/VIS (CHCl$_3$): $\lambda_{max}$ (ε)=472 (38220), 501 (50890) nm.

Analytical Data on Example 13:
Elemental analysis (% by weight calc./found): C: 78.2/78.0; H: 5.2/5.2; N: 9.4/9.4; O: 7.2/7.4;
Mass (FD, 8 kV): m/z=445.3 [M+, 100%];
IR (KBr): ν=2199 (m, C≡N), 1678 (s, C=O), 1650 (s, C=O) cm$^{-1}$;
UV/VIS (CHCl$_3$): $\lambda_{max}$ (ε)=471 (37600), 496 (50330) nm.

Analytical Data on Example 14:
Elemental analysis (% by weight calc./found): C: 79.8/79.7; H: 3.9/3.9; N: 6.0/6.0; O: 10.3/10.4;
Mass (FD, 8 kV): m/z=466.4 [M+, 100%];
IR (KBr): ν=2200 (m, C≡N), 1682 (s, C=O), 1652 (s, C=O) cm$^{-1}$;
UV/VIS (CHCl$_3$): $\lambda_{max}$ (ε)=473 (37130), 504 (46220) nm.

Analytical Data on Example 15:
Elemental analysis (% by weight calc./found): C: 79.8/79.6; H: 3.9/3.9; N: 6.0/6.0; O: 10.3/10.5;
Mass (FD, 8 kV): m/z=466.3 [M+, 100%];
IR (KBr): ν=2200 (m, C≡N), 1683 (s, C=O), 1651 (s, C=O) cm$^{-1}$;
UV/VIS (CHCl$_3$): $\lambda_{max}$ (ε)=473 (37200), 503 (46340) nm.

Analytical Data on Example 16:
Elemental analysis (% by weight calc./found): C: 69.3/69.2; H: 2.8/2.8; N: 5.55/5.6; O: 15.95/6.0; S: 6.4/6.4;
Mass (FD, 8 kV): m/z=502.3 [M+, 100%];
IR (KBr): ν=2202 (m, C≡N), 1678 (s, C=O), 1651 (s, C=O) cm$^{-1}$;
UV/VIS (C$_2$H$_2$Cl$_4$): $\lambda_{max}$ (ε)=473 (36870), 504 (45630) nm.

d) Preparation of the 9-cyanoperylene-3,4-dicarboxylic imides Ib

Examples 17 to 23 x g (10 mmol) of the monofunctional 9-cyanoperylene-3,4-dicarboxylic imide Ib from Examples 12 to 15 were dissolved with stirring in $v_1$ ml of the diluent VM and $v_2$ ml of the base B and heated to the desired reaction temperature T° C. A solution of y g (Y mmol) of the carbonyl chloride V in $v_3$ ml of the diluent VM was then slowly added dropwise and the reaction mixture was stirred at the reaction temperature for a further t h. After the reaction had been ended, the solvent was removed distillatively at 60° C. (50° C. in Example 17) under reduced pressure, the residue was dissolved in very little chloroform and subjected to a column filtration through silica gel as the stationary phase and chloroform as the mobile phase. Finally, the solvent was removed under reduced pressure.

Further details on these experiments and also their results are compiled in Table 3.

In the table:

TABLE 3

| Ex. | x [g] | Ia from Ex. | $v_1$ [ml] | Diluent VM | $v_2$ [ml] | Base B | $v_3$ [ml] | y [g] | Y [mmol] | Acid chloride V | t [h] | T [° C.] | Yield [g/%] | Appearance |
|---|---|---|---|---|---|---|---|---|---|---|---|---|---|---|
| 17 | 4.3 | 12 | — | Dioxane | 100 | Pyridine | 50 | 1.35 | 15 | AC | 2 | 55 | 2.8/58 | red-brown, amorphous |
| 18 | 4.3 | 12 | — | Dioxane | 100 | Pyridine | 50 | 1.35 | 13 | MAC | 1.5 | 80 | 3.95/79 | brown-red, microcryst. |
| 19 | 4.3 | 12 | 100 | Dioxane | 5 | DBU | 50 | 1.35 | 13 | MAC | 1.5 | 80 | 3.5/70 | brown-red, microcryst. |
| 20 | 4.3 | 12 | 100 | DMF | 10 | Pyridine | 30 | 1.6 | 15 | MAC | 1.5 | 80 | 3.65/73 | brown-red, amorphous |

TABLE 3-continued

| Ex. | x [g] | Ia from Ex. | v₁ [ml] | Diluent VM | v₂ [ml] | Base B | v₃ [ml] | y [g] | Y [mmol] | Acid chloride V | t [h] | T [° C.] | Yield [g/%] | Appearance |
|---|---|---|---|---|---|---|---|---|---|---|---|---|---|---|
| 21 | 4.45 | 13 | — | Dioxane | 100 | Pyridine | 50 | 2.1 | 20 | MAC | 1.5 | 80 | 3.8/74 | brown, amorphous |
| 22 | 4.65 | 14 | — | Dioxane | 150 | Pyridine | 50 | 2.1 | 20 | MAC | 1.5 | 80 | 4.35/81 | red-orange, microcryst. |
| 23 | 4.65 | 15 | — | Dioxane | 150 | Pyridine | 50 | 2.6 | 25 | MAC | 2 | 80 | 4.45/83 | brown-orange, microcryst. |

DMF: N,N-Dimethylformamide
DBU: Diazabicycloundecene
AC: Acrylic chloride
MAC: Methacrylic chloride Analytical Data on Example 17:
Elemental analysis (% by weight calc./found): C: 76.55/76.5; H: 4.55/4.5; N: 5.75/5.8; O: 13.15/13.2;
Mass (FD, 8 kV): m/z=486.4 [M⁺, 100%];
IR (KBr): ν=2200 (m, C≡N), 1680 (s, C=O), 1650 (s, C=O) cm⁻¹;
UV/VIS (CHCl₃): $\lambda_{max}$ (ϵ)=472 (37550), 501 (49980) nm.

Analytical Data on Example 18:
Elemental analysis (% by weight calc./found): C: 76.8/76.8; H: 4.8/4.8; N: 5.6/5.6; O: 12.8/12.8;
Mass (FD, 8 kV): m/z=500.4 [M⁺, 100%];
IR (KBr): ν=2200 (m, C≡N), 1680 (s, C=O), 1649 (s, C=O) cm⁻¹;
UV/VIS (CHCl₃): $\lambda_{max}$ (ϵ)=472 (36970), 501 (49560) nm.

Analytical Data on Example 21:
Elemental analysis (% by weight calc./found): C: 77.15/77.0; H: 5.3/5.3; N: 8.2/8.25; O: 9.35/9.45;
Mass (FD, 8 kV): m/z=513.5 [M⁺, 100%];
IR (KBr): ν=2198 (m, C≡N), 1682 (s, C=O), 1651 (s, C=O) cm⁻¹;
UV/VIS (CHCl₃): $\lambda_{max}$ (ϵ)=472 (36440), 502 (48980) nm.

Analytical Data on Example 22:
Elemental analysis (%.by weight calc./found):
C: 78.65/78.5; H: 4.15/4.2; N: 5.25/5.3; O: 11.95/12.0;
Mass (FD, 8 kV): m/z=534.5 [M⁺, 100%];
IR (KBr): ν=2200 (m, C≡N), 1682 (s, C=O), 1651 (s, C=O) cm⁻¹;
UV/VIS (CHCl₃): $\lambda_{max}$ (ϵ)=473 (35090), 504 (46720) nm.

Analytical Data on Example 23:
Elemental analysis (% by weight calc./found): C: 78.65/78.4; H: 4.15/4.2; N: 5.25/5.3; O: 11.95/12.1;
Mass (FD, 8 kV): m/z=534.4 [M⁺, 100%];
IR (KBr): ν=2200 (m, C≡N), 1683 (s, C=O), 1650 (s, C=O) cm⁻¹;
UV/VIS (CHCl₃): $\lambda_{max}$ (ϵ)=473 (34990), 503 (46530) nm.

Preparation of the 9-cyanoperylene-3,4-dicarboxylic imides Ic

Examples 24 to 30

A mixture of x g (0.1 mol) of 9-bromoperylene-3,4-dicarboximide VI, y g (Y mol) of copper(I) cyanide and v ml of diluent D, and also 50 g of pyridine as a catalyst in Example 30, was heated to the desired reaction temperature T° C. with stirring in a nitrogen atmosphere for t h. After the reaction mixture was cooled, it was diluted either with the same volume of methanol (Examples 24, 25, 27, 29) or else with 40% by volume of an ethanol/water mixture in a volume ratio of 1:1 (Examples 26, 28, 30), and the precipitated solid was filtered off, stirred in a mixture of 1000 ml of water, 150 ml of conc. hydrochloric acid and 100 g of iron(III) chloride to destroy excess copper(I) cyanide at 60° C. for 1 h and filtered again, and the residue was washed with hot water until the filtrate was neutral and almost colorless and dried at 120° C. under reduced pressure.

For purification, the crude product prepared in this way was dissolved in v' ml of N-methylpyrrolidone (NMP) at 80° C., admixed with 10 g of activated carbon, stirred at this temperature for a further 30 min and hot-filtered. After cooling to 60° C., the product was precipitated by adding 500 ml of 65% by volume ethanol, stirred at 60° C. for a further 3 h, slowly cooled to room temperature, filtered off, washed with ethanol to free it of NMP and dried.

Further details on these experiments and also their results are compiled in Table 4.

In the table:

TABLE 4

| Ex. | x [g] | VI | y [g] | Y [mol] | Diluent D | t [h] | T [° C.] | v' [ml] | Yield [g/%] | Appearance | m.p. [° C.] |
|---|---|---|---|---|---|---|---|---|---|---|---|
| 24 | 56.8 | 9-Bromo-N-dodecylperylene-dicarboximide | 22.4 | 0.25 | Sulfolane | 1 | 275 | 500 | 42.7/83 | red-brown, microcryst. | 220-221 |
| 25 | 52.6 | 9-Bromo-N-(5-nonyl)-perylenedicarboximide | 22.4 | 0.25 | Sulfolane | 1 | 275 | 500 | 35.4/75 | red-orange, amorphous | 203-204 |
| 26 | 48.2 | 9-Bromo-N-cyclohexylperylene-dicarboximide | 11.6 | 0.13 | NMP | 3 | 200 | 450 | 33.4/78 | red-orange, amorphous | >300 |
| 27 | 56.0 | 9-Bromo-N-(2,6-diisopropylphenyl)perylenedicarboximide | 22.4 | 0.25 | Sulfolane | 1 | 275 | 700 | 40.5/80 | orange-red, microcryst. | >300 |
| 28 | 56.0 | 9-Bromo-N-(2,6-diisopropylphenyl)perylenedicarboximide | 11.6 | 0.13 | NMP | 3 | 200 | 675 | 37.9/75 | orange-red, microcryst. | >300 |

TABLE 4-continued

| Ex. | x [g] | VI | y [g] | Y [mol] | Diluent D | t [h] | T [°C.] | v' [ml] | Yield [g/%] | Appearance | m.p. [°C.] |
|---|---|---|---|---|---|---|---|---|---|---|---|
| 29 | 58.8 | 9-Bromo-N-(2,5-di-tert-butylphenyl)-perylenedicarboximide | 22.4 | 0.25 | Sulfolane | 1 | 275 | 600 | 43.3/81 | orange, microcryst. | >300 |
| 30 | 46.6 | 9-Bromo-N-(p-meth-oxy-benzyl)perylenedicarboximide | 17.9 | 0.20 | DMAc | 4 | 165 | 650 | 35.9/77 | orange-red, microcryst. | >300 |

NMP: N-Methylpyrrolidone
DMAc: N,N-Dimethylacetamide

Analytical Data on Example 26:
Elemental analysis (% by weight calc./found): C: 81.3/81.1; H: 4.7/4.7; N: 6.55/6.6; O: 7.45/7.6;
Mass (FD, 8 kV): m/z=428.2 [M$^+$, 100%];
IR (KBr): ν=2200 (m, C≡N), 1684 (s, C=O), 1649 (s, C=O) cm$^{-1}$;
UV/VIS (CHCl$_3$): $\lambda_{max}$ (ε)=475 (37100), 502 (48530) nm.

We claim:
1. A 9-cyano-substituted perylene-3,4-dicarboxylic monoimide of the general formula I

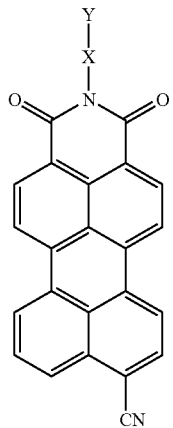

where the variables are defined as follows:
X is a chemical bond;
C$_1$-C30-alkylene whose carbon chain may be interrupted by one or more —O—, —S—, —NR$^1$, —CO— and/or —SO$_2$— moieties, and which may be substituted by —COOR$^1$, —SO$_3$R$^1$, cyano, C$_1$-C$_6$-alkoxy, aryl which may be substituted by C$_1$-C$_{18}$-alkyl and/or C$_1$-C$_6$-alkoxy, and/or be mono- or polysubstituted by a 5- to 7-membered heterocyclic radical which is bonded via a nitrogen atom and may contain further heteroatoms and be aromatic; C$_5$-C$_8$-cycloalkylene whose carbon framework may be interrupted by one or more —O—, —S—, —NR$^1$—, —CO— and/or —SO$_2$— moieties and/or may be mono- or polysubstituted by C$_1$-C12-alkyl, —COOR$^1$, —SO$_3$R$^1$, cyano and/or C,-C6-alkoxy;
arylene or hetarylene, each of which may be mono- or polysubstituted by C$_1$-C$_{18}$-alkyl, C$_1$-C$_6$-alkoxy, cyano, —COOR$^1$, —SO$_3$R$^1$, —CONH—R$^1$ and/or —NH—COR$^1$;
C$_1$-C$_{20}$-alkylarylene or -hetarylene whose alkylene group may in each case be interrupted by one or more —O—, —S—, —NR$^1$—, —CO— and/or —SO$_2$— moieties and which may in each case be mono- or polysubstituted by —COOR$^1$, —SO$_3$R$^1$, —CONHR$^1$, —NHCOR$^1$, cyano, C$_1$-C$_{18}$-alkyl, C$_1$-C$_6$-alkoxy and/or a 5- to 7-membered heterocyclic radical which is bonded via a nitrogen atom and may contain further heteroatoms and be aromatic;
aryl- or hetaryl-C$_1$-C$_{20}$-alkylene, whose alkylene group may in each case be interrupted by one or more —O—, —S—, —NR$^1$—, —CO— and/or -5O2- moieties and which may each be mono- or polysubstituted by —COOR$^1$, —SO$_3$R$^1$, —CONHR$^1$, —NHCOR$^1$, cyano, C$_1$-C$_{18}$-alkyl, C$_1$-C$_6$-alkoxy and/or a 5- to 7-membered heterocyclic radical which is bonded via a nitrogen atom and may contain further heteroatoms and be aromatic;
Y is a functional group Y' or a polymerizable group P; or
X—Y together is an R radical;
Y' is amino, hydroxyl, —COOH, —SO$_3$H, chlorine or bromine;
P is a radical of the general formula II

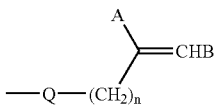

A,B
are each independently hydrogen, C$_1$-C$_6$-alkyl or phenyl, or are together a cyclopentene or cyclohexene ring which contains the double bond to which A and B are bonded;
Q is a chemical bond;
an —O—, —NR$^2$—, —S—, —OCO—, —OCOO—, —OCONR$^3$—, —NR$^3$CO—, —NR$^3$COO—, —NR$^3$CONR$^4$—, —CO—, —COO—, —CONR$^3$—, —SO$_2$—O—, —SO$_2$NR$^3$—, —O—SO$_2$— or —NR$^3$SO$_2$— moiety;
n is 0, 1, 2 or 3;
R is hydrogen;
C$_1$-C$_{30}$-alkyl whose carbon chain may be interrupted by one or more —O—, —S—, —NR$^1$, —CO— and/or —SO$_2$— moieties, and which may be substituted by cyano, C$_1$-C$_6$-alkoxy, aryl which may be substituted by C$_1$-C$_{18}$-alkyl and/or C$_1$-C$_6$-alkoxy, and/or be mono- or polysubstituted by a 5- to 7-membered heterocyclic radical which is bonded via a nitrogen atom and may contain further heteroatoms and be aromatic;
C$_5$-C$_8$-cycloalkyl whose carbon framework may be interrupted by one or more —O—, —S— and/or —NR$^1$— moieties and/or may be mono- or polysubstituted by C$_1$-C$_6$-alkyl;
aryl or hetaryl, each of which may be mono- or polysubstituted by C$_1$-C$_{18}$-alkyl, C$_1$-C$_6$-alkoxy, cyano, —CONHR$^5$, —NHCOR$^5$ and/or aryl- or hetarylazo, each of which may be substituted by C$_1$-C$_{10}$-alkyl, C$_1$-C$_6$-alkoxy and/or cyano;
R$^1$ is hydrogen or C$_1$-C$_6$-alkyl;
R$^2$ is hydrogen, C$_1$-C$_6$-alkyl, aryl, aryl-C$_1$-C$_6$-alkyl, C$_1$-C$_6$-alkylcarbonyl, arylcarbonyl or formyl;

R³, R⁴
  are each independently hydrogen; $C_1$-$C_6$-alkyl; aryl or aryl-$C_1$-$C_6$-alkyl, each of which may be substituted by hydroxyl, halogen, $C_1$-$C_6$-alkyl and/or $C_1$-$C_6$-alkoxy;

R⁵
  is hydrogen; $C_1$-$C_{18}$-alkyl; aryl or hetaryl, each of which may be substituted by $C_1$-$C_6$-alkyl, $C_1$-C6-alkoxy, halogen, hydroxyl, carboxyl and/or cyano.

2. A perylene-3,4-dicarboxylic monoimide of the general formula I as claimed in claim 1, in which the variables are defined as follows:

X
  is $C_1$-$C_{30}$-alkylene, whose carbon chain may be interrupted by one or more —O— and/or —CO— moieties, and which may be substituted by —COOR¹, cyano, $C_1$-$C_6$-alkoxy and/or aryl which may be substituted by $C_1$-$C_{18}$-alkyl and/or $C_1$-$C_6$-alkoxy;
  $C_5$-$C_8$-cycloalkylene which may be mono- or polysubstituted by $C_1$-$C_{12}$-alkyl, —COOR¹, cyano and/or $C_1$-$C_6$-alkoxy;
  arylene or hetarylene, each of which may be mono- or polysubstituted by $C_1$-$C_{18}$-alkyl, $C_1$-$C_6$-alkoxy, cyano, —COOR¹, —CONH—R¹ and/or —NH-COR¹;
  $C_1$-$C_{20}$-alkylarylene or -hetarylene whose alkylene group may in each case be interrupted by one or more —O— and/or —CO— moieties and which may in each case be mono- or polysubstituted by —COOR¹, cyano, $C_1$-$C_{18}$-alkyl and/or $C_1$-$C_6$-alkoxy; aryl - or hetaryl-$C_1$-$C_{20}$-alkylene, whose alkylene group may in each case be interrupted by one or more —O— and/or —CO— moieties and which may in each case be mono- or polysubstituted by —COOR¹, cyano, $C_1$-$C_{18}$-alkyl and/or $C_1$-$C_6$-alkoxy;

Y is a functional group Y' or a polymerizable group P; or
X—Y together is an R radical;
Y' is amino, hydroxyl, —COOH or bromine;
P is a radical of the general formula IL

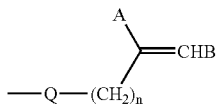

II

A,B
  are each independently hydrogen, $C_1$-C6-alkyl or phenyl, or are together a cyclopentene or cyclohexene ring which contains the double bond to which A and B are bonded;
Q is a chemical bond;
  a —O—, —NR²—, —OCO—, —NR³CO—, —COO— or —CONR— moiety;
n is 0, 1, 2 or 3;
R is hydrogen;
  $C_1$-$C_{30}$-alkyl whose carbon chain may be interrupted by one or more —O—, —NR¹— and/or —CO— moieties, and which may be substituted by cyano, $C_1$-$C_6$-alkoxy, aryl which may be substituted by $C_1$-$C_{18}$-alkyl and/or $C_1$-$C_6$-alkoxy, and/or be mono- or polysubstituted by a 5- to 7-membered heterocyclic radical which is bonded via a nitrogen atom and may contain further heteroatoms and be aromatic;
  $C_5$-$C_8$-cycloalkyl whose carbon framework may be interrupted by one or more —O— and/or —NR¹— moieties and/or may be mono- or polysubstituted by $C_1$-$C_6$-alkyl;
  aryl or hetaryl, each of which may be mono- or polysubstituted by $C_1$-$C_{18}$-alkyl, $C_1$-$C_6$-alkoxy, cyano and/or aryl- or hetarylazo, each of which may be substituted by C1-$C_{10}$-alkyl, $C_1$-$C_6$-alkoxy and/or cyano;

R¹ is hydrogen or $C_1$-$C_6$-alkyl;
R² is hydrogen, $C_1$-$C_6$-alkyl, aryl, aryl-$C_1$-$C_6$-alkyl;
R³
  is hydrogen; $C_1$-$C_6$-alkyl; aryl or aryl-$C_1$-$C_6$-alkyl, each of which may be substituted by hydroxyl, $C_1$-$C_6$-alkyl and/or $C_1$-$C_6$-alkoxy.

3. A process for preparing perylene-3,4-dicarboxylic monoimides of the general formula Ia

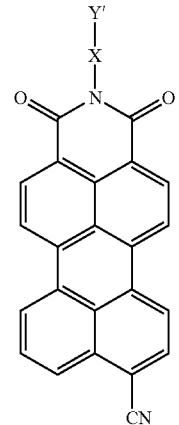

Ia

B where
X is a chemical bond;
  $C_1$-$C_{30}$-alkylene whose carbon chain may be interrupted by one or more —O—, —S—, —NR¹—, —CO— and/or —SO₂— moieties, and which may be substituted by —COOR¹, —SO₃R¹, cyano, $C_1$-$C_6$-alkoxy, aryl which may be substituted by $C_1$-$C_{18}$-alkyl and/or $C_1$-$C_6$-alkoxy, and/or be mono- or polysubstituted by a 5- to 7-membered heterocyclic radical which is bonded via a nitrogen atom and may contain further heteroatoms and be aromatic: $C_5$-$C_8$-cycloalkylene whose carbon framework may be interrupted by one or more —O—, —S—, —NR¹—, —CO— and/or —SO₂— moieties and/or may be mono- or polysubstituted by $C_1$-$C_{12}$-alkyl, —COOR¹, —SO₃R¹, cyano and/or $C_1$-$C_6$-alkoxy;
  arylene or hetarylene, each of which may be mono- or polysubstituted by $C_1$-$C_{18}$-alkyl, $C_1$-$C_6$-alkoxy, cyano, —COOR¹, —SO₃R¹, —CONH—R¹ and/or —NH—COR¹;
  $C_1$-$C_{20}$-alkylarylene or -hetarylene whose alkylene group may in each case be interrupted by one or more —O—, —S—, —NR¹—, —CO— and/or —SO₂— moieties and which may in each case be mono- or polysubstituted by —COOR¹, —SO₃R¹, —CONHR¹, —NHCOR¹, cyano, $C_1$-$C_{18}$-alkyl, $C_1$-$C_6$-alkoxy and/or a 5- to 7-membered heterocyclic radical which is bonded via a nitrogen atom and may contain further heteroatoms and be aromatic;
  aryl- or hetaryl-$C_1$-$C_{20}$-alkylene, whose alkylene group may in each case be interrupted by one or more —O—, —S—, —NR—, —CO— and/or —SO₂— moieties and which may each be mono- or polysubstituted by —COOR¹, —SO₃R¹, —CONHR¹, —NH-COR¹, cyano, $C_1$-$C_{18}$-alkyl, $C_1$-$C_6$-alkoxy and/or a 5- to 7-membered heterocyclic radical which is bonded via a nitrogen atom and may contain further heteroatoms and be aromatic;

Y' is amino, hydroxyl, —COOH, —SO₃H, chlorine or bromine;
B or X—Y' together are R;
R is hydrogen;

$C_1$-$C_{30}$-alkyl whose carbon chain may be interrupted by one or more —O—, —S—, —NR$^1$—, —CO— and/or —SO$_2$— moieties, and which may be substituted by cyano, $C_1$-$C_6$-alkoxy, aryl which may be substituted by $C_1$-$C_{18}$-alkyl and/or $C_1$-$C_6$-alkoxy, and/or be mono - or polysubstituted by a 5- to 7-membered heterocyclic radical which is bonded via a nitrogen atom and may contain further heteroatoms and be aromatic;

$C_5$-$C_8$-cycloalkyl whose carbon framework may be interrupted by one or more —O—, —S— and/or —NR$^1$— moieties and/or may be mono- or polysubstituted by $C_1$-$C_6$-alkyl;

aryl or hetaryl, each of which may be mono- or polysubstituted by $C_1$-$C_{18}$-alkyl, $C_1$-$C_6$-alkoxy, cyano, —CONHR$^5$, —NHCOR$^5$ and/or aryl- or hetarylazo, each of which may be substituted by $C_1$-$C_{10}$-alkyl, $C_1$-$C_6$-alkoxy and/or cyano;

R$^1$ is hydrogen or $C_1$-$C_6$-alkyl;

R$^5$ is hydrogen; $C_1$-$C_{18}$-alkyl; aryl or hetaryl, each of which may be substituted by $C_1$-$C_{6\text{-}alkyl}$, $C_1$-$C_6$-alkoxy, halogen, hydroxyl, carboxyl and/or cyano, which comprises a) brominating perylene-3,4-dicarboxylic anhydride in the 9-position using elemental bromine in concentrated sulfuric acid or an aliphatic monocarboxylic acid, b) reacting the 9-bromoperylene-3,4-dicarboxylic anhydride obtained in step a) with copper(I) cyanide in excess in a high-boiling inert diluent, optionally with the addition of a basic nitrogen compound or of a nitrogen heterocycle as a catalyst, and c) reacting the 9-cyanoperylene-3,4-dicarboxylic anhydride obtained in step b) with a primary amine of the general formula IV

Y'—X—NH$_2$    IV in water or an inert organic solvent, optionally with the addition of an imidation catalyst, to give the desired 9-cyanoperylene-3,4-dicarboxylic monoimide of the formula Ia.

4. A process for preparing perylene-3,4-dicarboxylic monoimides of the general formula Ib

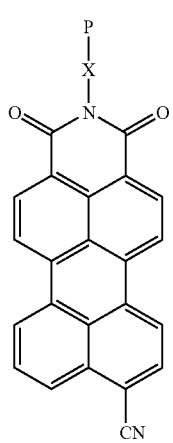

B where X is as defined in claim 3 and P is a radical of the general formula II

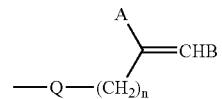

A,B are each independently hydrogen, $C_1$-$C_6$-alkyl or phenyl, or are together a cyclopentene or cyclohexene ring which contains the double bond to which A and B are bonded;

n is 0, 1, 2 or 3;

where Q is —OCO— or —NHCO—, which comprises reacting a perylene-3,4-dicarboxylic monoimide of the formula Ia as defined in claim 3 where Y' is amino or hydroxyl with a carbonyl chloride of the general formula V

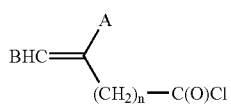

in an inert aprotic diluent, with the addition of a nitrogen base.

5. A process for preparing perylene-3,4-dicarboxylic monoimides of the general formula Ic

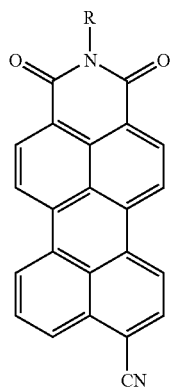

where R is hydrogen;

$C_1$-$C_{30}$-alkyl whose carbon chain may be interrupted by one or more —O—, —S—, —NR—, —CO— and/or —SO$_2$— moieties, and which may be substituted by cyano. $C_1$-$C_6$-alkoxy, aryl which may be substituted by $C_1$-$C_{18}$-alkyl and/or $C_1$-$C_6$-alkoxy, and/or be mono - or polysubstituted by a 5- to 7-membered heterocyclic radical which is bonded via a nitrogen atom and may contain further heteroatoms and be aromatic;

$C_5$-$C_8$-cycloalkyl whose carbon framework may be interrupted by one or more —O—, —S— and/or —NR$^1$— moieties and/or may be mono- or polysubstituted by $C_1$-$C_6$-alkyl;

aryl or hetaryl, each of which may be mono- or polysubstituted by $C_1$-$C_{18}$-alkyl, C1-$C_6$-alkoxy,cyano, —CONHR$^5$, —NHCOR$^5$ and/or aryl- or hetarylazo, each of which may be substituted by $C_1$-$C_{10}$-alkyl, $C_1$-$C_6$-alkoxy and/or cyano;

R$^1$ is hydrogen or $C_1$-$C_6$-alkyl;

$R^5$
is hydrogen; $C_1$-$C_{18}$-alkyl; aryl or hetaryl, each of which may be substituted by C 1-$C_6$-alkyl, $C_1$-$C_6$-alkoxy, halogen, hydroxyl, carboxyl and/or cyano, which comprises converting a 9-bromoperylene-3,4-dicarboxylic monoimide of the general formula VI

VI

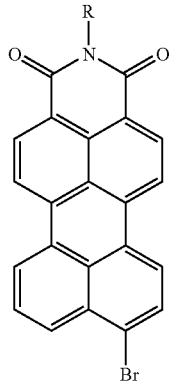

to the desired 9-cyanoperylene-3,4-dicarboxylic monoimide of the formula Ic by reacting with copper (I) cyanide without a diluent or in a high-boiling inert diluent, optionally with the addition of a basic nitrogen compound or of a nitrogen heterocycle as a catalyst.

6. A method for coloring high molecular weight organic and inorganic materials comprising utilizing the 9-cyano-substituted perylene-3,4-dicarboxylic monoimides of the general formula I as claimed in claim 1 as a colorant.

7. The method as claimed in claim 6, wherein plastics, paints, printing inks, inorganic-organic composites and oxidic layer systems are colored.

8. A composition comprising the 9-cyano-substituted perylene-3,4-dicarboxylic monoimide of the general formula I as claimed in claim 1 wherein said composition is a dispersant, a pigment additive for organic pigments and an intermediate for the preparation of fluorescent dyes and pigment additives.

9. A method for producing aqueous polymer dispersions and inkjet inks absorbing and/or emitting in the yellow region of the electromagnetic spectrum comprising utilizing the 9-cyano-substituted perylene-3,4-dicarboxylic monoimides of the general formula I as claimed in claim 1.

10. A composition comprising the 9-cyano-substituted perylene-3,4-dicarboxylic monoimide of the general formula I as claimed in claim 1 wherein said composition is a coloring or color-correcting component in emissive and transflective color filters and in retroreflective components.

11. A composition comprising the 9-cyano-substituted perylene-3,4-dicarboxylic monoimide of the general formula I as claimed in claim 1 wherein said composition is a photoconductor in electrophotography, an emitter in electroluminescence and chemiluminescence applications, an active component in fluorescence conversion, in bioluminescence arrays and in photovoltaics and a laser dye.

* * * * *